(12) United States Patent
Ozaki

(10) Patent No.: US 7,583,775 B2
(45) Date of Patent: Sep. 1, 2009

(54) CONCENTRATED IRRADIATION TYPE RADIOTHERAPY APPARATUS

(75) Inventor: Masahiro Ozaki, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/640,355

(22) Filed: Aug. 14, 2003

(65) Prior Publication Data

US 2004/0034269 A1 Feb. 19, 2004

(30) Foreign Application Priority Data

| Aug. 14, 2002 | (JP) | ............................. 2002-236504 |
| Aug. 14, 2002 | (JP) | ............................. 2002-236505 |
| Aug. 14, 2002 | (JP) | ............................. 2002-236506 |

(51) Int. Cl.
G21G 1/12 (2006.01)

(52) U.S. Cl. .................. 376/157; 376/156; 250/370.11; 250/505.1; 378/152; 378/65

(58) Field of Classification Search ................ 376/157, 376/156; 250/370.11, 505.1; 378/152, 65
See application file for complete search history.

(56) References Cited

U.S. PATENT DOCUMENTS

| 4,463,266 A | * | 7/1984 | Brahme | .................... 250/505.1 |
| 4,868,843 A | * | 9/1989 | Nunan | ......................... 378/152 |
| 4,882,741 A | * | 11/1989 | Brown | ......................... 378/152 |
| 5,250,019 A | * | 10/1993 | McGinley | ....................... 600/1 |
| 5,591,983 A | * | 1/1997 | Yao | ........................... 250/505.1 |
| 5,673,300 A | | 9/1997 | Reckwerdt et al. | |
| 5,724,400 A | * | 3/1998 | Swerdloff et al. | ............... 378/65 |
| 5,889,834 A | * | 3/1999 | Vilsmeier et al. | ............ 378/147 |
| 6,335,961 B1 | * | 1/2002 | Wofford et al. | ................ 378/65 |
| 6,385,288 B1 | | 5/2002 | Kanematsu | |
| 6,449,340 B1 | * | 9/2002 | Tybinkowski et al. | ........ 378/150 |
| 6,526,123 B2 | * | 2/2003 | Ein-Gal | ........................ 378/152 |
| 6,600,810 B1 | * | 7/2003 | Hughes | ........................ 378/152 |
| 6,822,252 B2 | * | 11/2004 | Svatos et al. | ............... 250/505.1 |

FOREIGN PATENT DOCUMENTS

| CN | 1345613 A | 4/2002 |
| JP | 56-8623 | 2/1981 |
| JP | 6-105922 | 4/1994 |
| JP | 10-113400 | 5/1998 |
| JP | 10-314323 | 12/1998 |
| JP | 10-328318 | 12/1998 |
| JP | 11-290309 | 10/1999 |
| JP | 2000-116638 | 4/2000 |
| JP | 2001-327514 | 11/2001 |
| JP | 2003-175117 | 6/2003 |

OTHER PUBLICATIONS

Merriam-Webster's Collegiate Dictionary, 10th Edition, p. 226.*

* cited by examiner

*Primary Examiner*—Rick Palabrica
(74) *Attorney, Agent, or Firm*—Oblon, Spivak, McClelland, Maier & Neustadt, P.C.

(57) ABSTRACT

A concentrated irradiation type radiotherapy apparatus comprises a radiation source, a multi-channeled radiation detector, a rotating mechanism, an image reconstruction unit, a multi-leaf collimator disposed between the radiation source and the subject to trim the radioactive rays in arbitrary shapes and including a plurality of first leaves and a plurality of second leaves each disposed to be individually movable forwards/backwards and each having a strip shape and in which types of the first leaves are different from those of the second leaves.

2 Claims, 26 Drawing Sheets

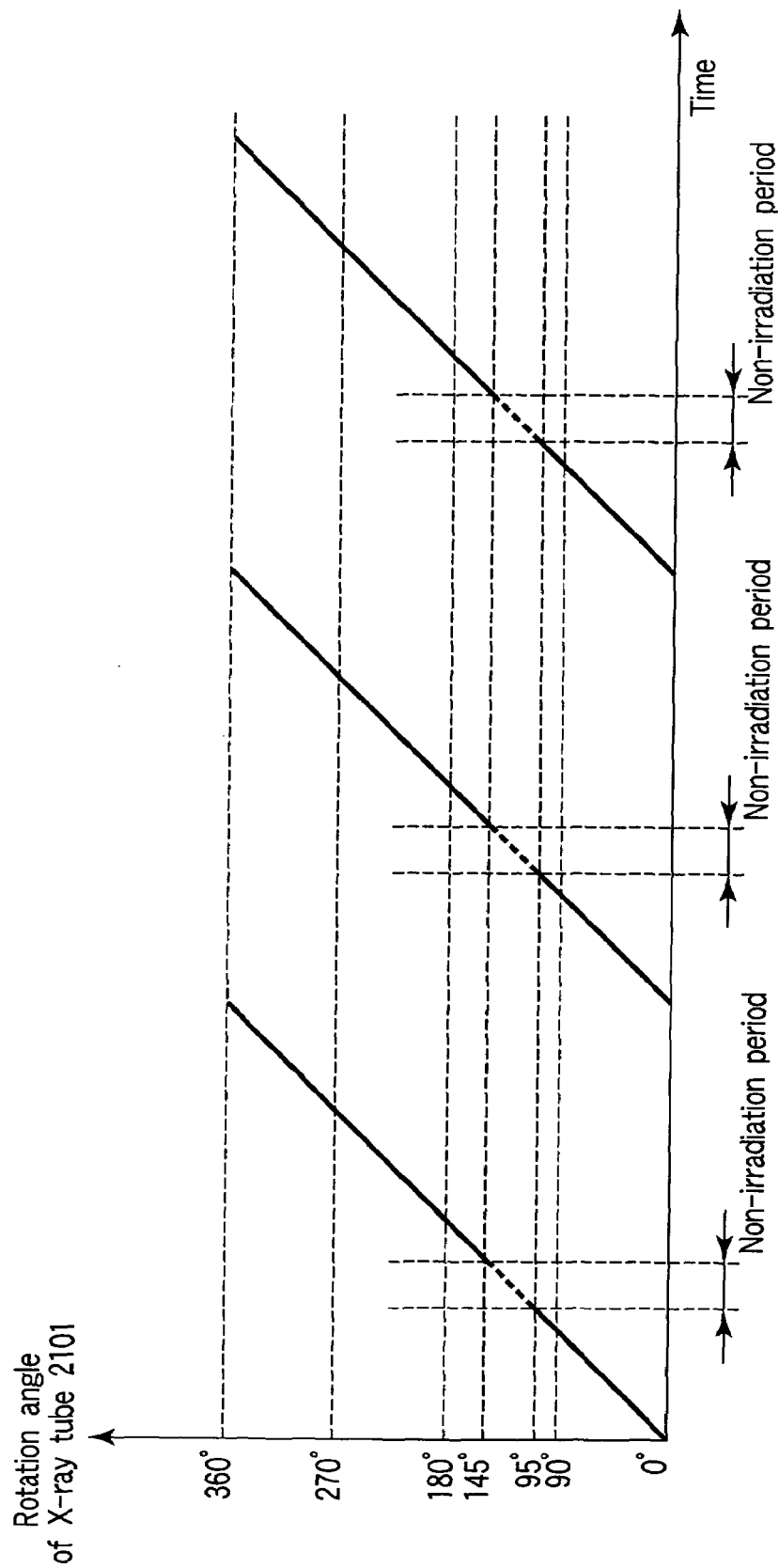
F I G. 21

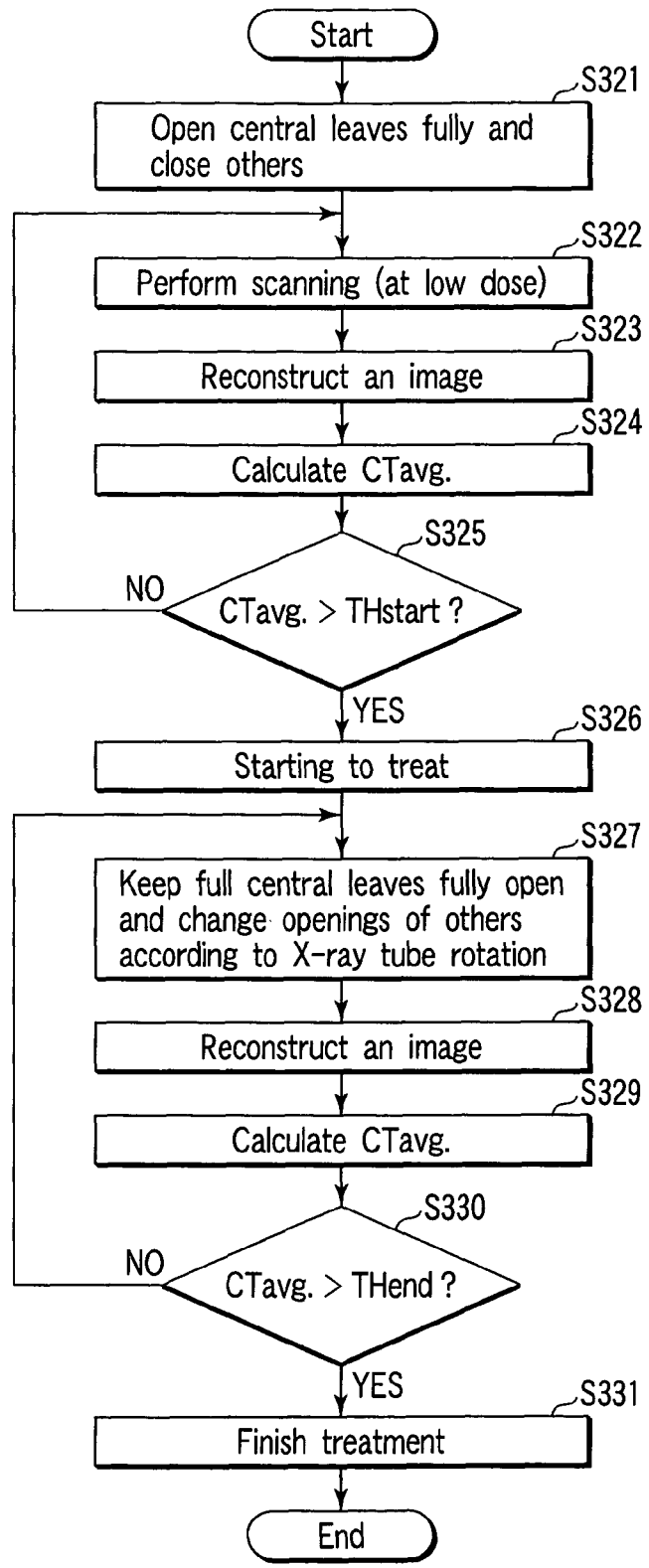
F I G. 35

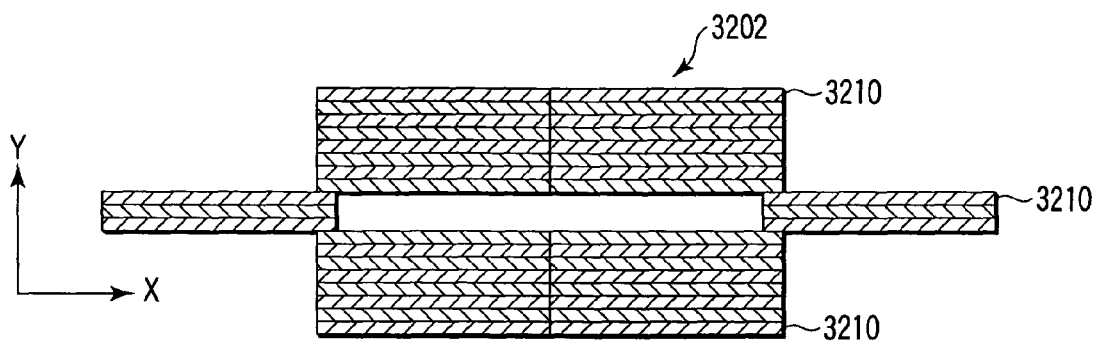
F I G. 36A
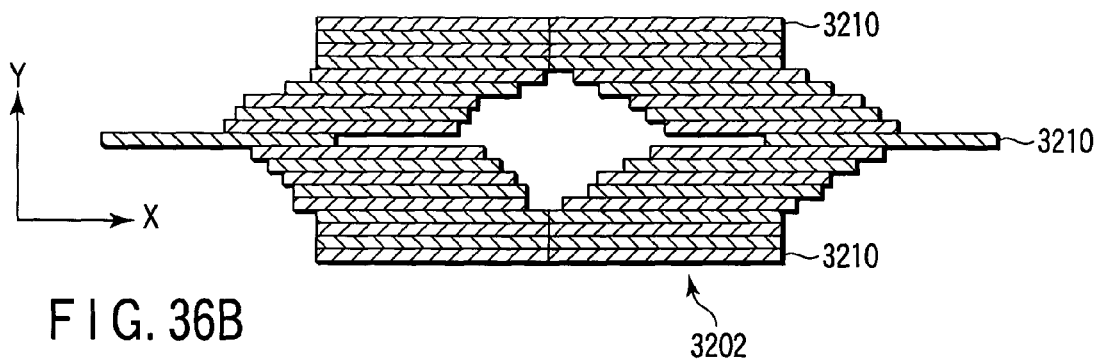
F I G. 36B
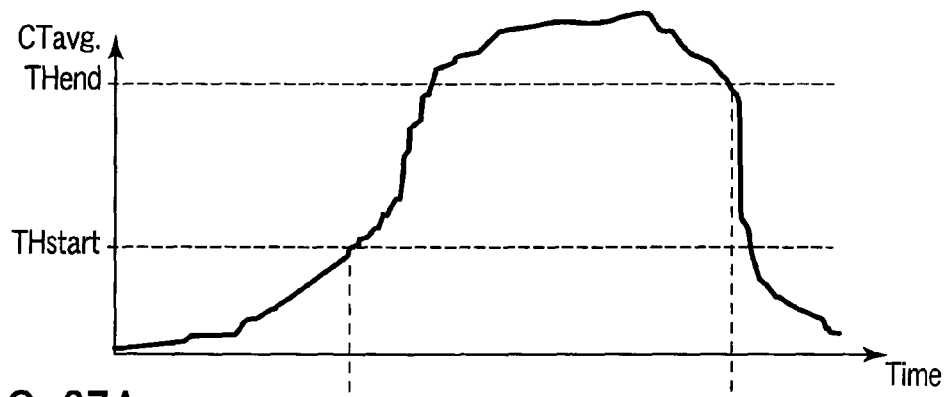
F I G. 37A
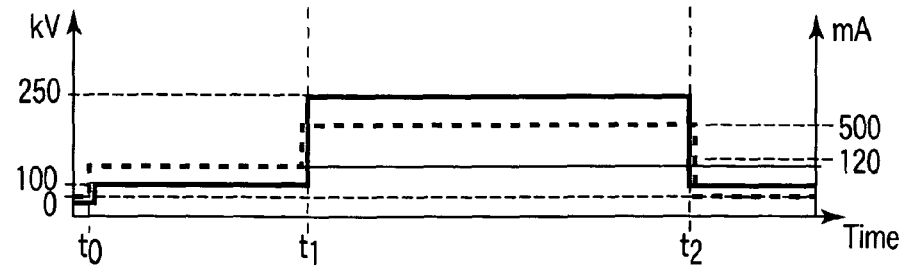
F I G. 37B

CONCENTRATED IRRADIATION TYPE RADIOTHERAPY APPARATUS

CROSS-REFERENCE TO RELATED APPLICATIONS

This application is based upon and claims the benefit of priority from the prior Japanese Patent Applications No. 2002-236504, filed Aug. 14, 2002; No. 2002-236505, filed Aug. 14, 2002; and No. 2002-236506, filed Aug. 14, 2002, the entire contents of all of which are incorporated herein by reference.

BACKGROUND OF THE INVENTION

1. Field of the Invention

The present invention relates to a concentrated irradiation type radiotherapy apparatus including an X-ray computer tomography function.

2. Description of the Related Art

An X-ray computer tomography apparatus reconstructs image data based on data transmitted through a subject. Diversion of the X-ray computer tomography apparatus to a concentrated irradiation type radiotherapy apparatus has been studied. For this, an X-ray tube is replaced with that having high-dose specifications. A multi-leaf collimator is added before the X-ray tube. The multi-leaf collimator includes a plurality of leaves which can individually move forwards/backwards. By forward/backward control of the leaves, it is possible to trim an X-ray in a shape in accordance with a shape of a treatment object.

For a conventional radiotherapy apparatus, the subject needs to be transferred to the radiotherapy apparatus from the X-ray computer tomography apparatus. The concentrated irradiation type radiotherapy apparatus carries out a series of operations from when an image for positioning starts to be acquired until the treatment ends. In the concentrated irradiation type radiotherapy apparatus, the subject does not have to be relocated.

Accordingly, reduction of a treatment time is realized. Since opportunities for causing positional deviation of the subject are reduced in a period from the positioning till start of the treatment, treatment precision is enhanced. Such superiority is peculiar, and this type of the concentrated irradiation type radiotherapy apparatus is assumed to further spread.

BRIEF SUMMARY OF THE INVENTION

A first object of the present invention is to provide a concentrated irradiation type radiotherapy apparatus in which a region to be treated can be confirmed together with an irradiation concentration region by an image during treatment.

A second object of the present invention is to provide a concentrated irradiation type radiotherapy apparatus in which both treatment efficiency and exposure reduction are realized.

A third object of the present invention is to reduce a time deviation of treatment start in the concentrated irradiation type radiotherapy apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

According to a aspect of the present invention, there is provided the concentrated irradiation type radiotherapy apparatus which comprises a radiation source, a multi-channeled radiation detector, a rotating mechanism, an image reconstruction unit, a multi-leaf collimator disposed between the radiation source and the subject to trim the radioactive rays in arbitrary shapes and including a plurality of first leaves and a plurality of second leaves each disposed to be individually movable forwards/backwards and each having a strip shape and in which types of the first leaves are different from those of the second leaves.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 21 is a diagram showing the X-ray non-irradiation period by the operation of S227 to S229 of FIG. 18 on a time axis;

FIG. 35 is a flowchart showing a series of flow till the treatment finish from the pre-scan in Embodiment 3-2;

FIGS. 36A, 36B are diagrams showing apertures of the multi-leaf collimators for S321 and S327 of FIG. 35;

FIGS. 37A, 37B are time charts showing changes of the CT value average in and after the pre-scan start and those of the tube voltage and current of the X-ray tube with the elapse of time in Embodiment 3-2.

DETAILED DESCRIPTION OF THE INVENTION

Figure 1:
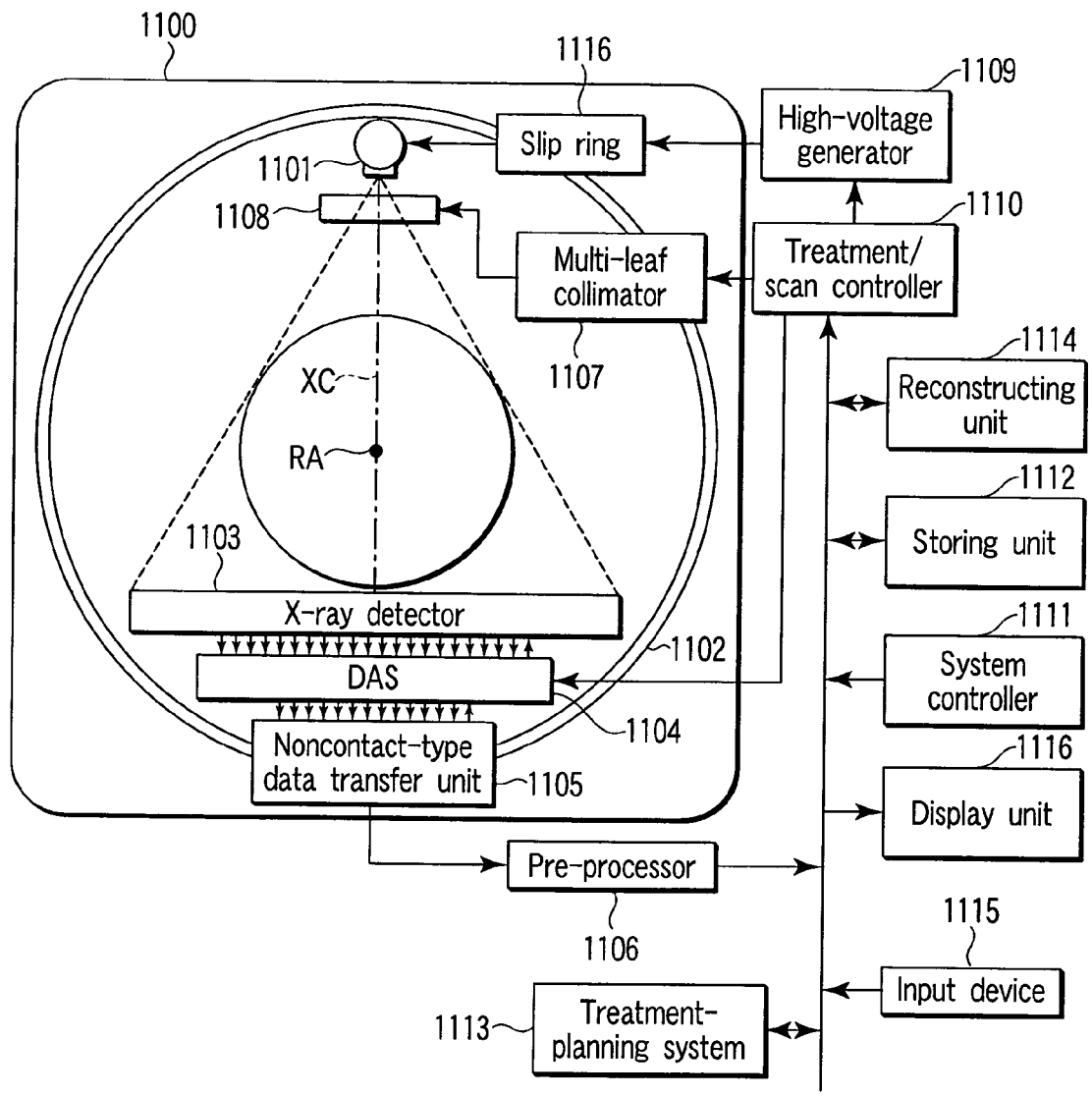
FIG. 1 is a diagram showing a constitution of a concentrated irradiation type radiotherapy apparatus according to a first embodiment of the present invention.

A concentrated irradiation type radiotherapy apparatus according to the present invention will be described hereinafter in terms of preferred embodiments with reference to the drawings. Radiant rays for treatment will be described as general X-rays, but are not limited to these. For the concentrated irradiation type radiotherapy apparatus, an aperture of a collimator is dynamically controlled in conjunction with continuous movement of a radiation source with respect to a subject (patient), and finely narrowed radioactive rays are constantly concentrated on a part to be treated of the subject. Accordingly, a treatment effect is selectively given to the part to be treated with a high energy, and exposure to another healthy part is minimized in the treatment apparatus. Here, an example in which the radiation source moves on a circumferential orbit will be described, but the moving orbit of the radiation source is not limited to this.

In this example, the concentrated irradiation type radiotherapy apparatus includes a basic structure common to that of an X-ray computer tomography apparatus. For the concentrated irradiation type radiotherapy apparatus, in the same manner as in the X-ray computer tomography apparatus, there are various types such as a rotation/rotation type in which an X-ray tube and radiation detector rotate as one unit around the subject, and a fixed/rotation type in which a large number of detection devices are arrayed in an annular form and only the X-ray tube rotates around the subject, and the present invention can be applied to any type. Here, the rotation/rotation type will be described. To reconstruct tomographic image data for one slice, projection data for one circumference of the subject of about 360° is required. Even in a half scan method, the projection data for 180°+fan angle is required. The present invention can be applied to any reconstruction method. Here, the half scan method advantageous in time resolution will be described as an example. For a mechanism for converting an incident X-ray to an electric charge, mainstreams are an indirect conversion system for converting the X-ray to light by a fluorescent member such as a scintillator and further converting the light to the electric charge by photoelectric conversion devices such as a photodiode, and a direct conversion system in which generation of electron/hole pairs in a semiconductor by the X-rays and movement of the pairs into electrodes, that is, photoconductive phenomenon is used. As an X-ray detection device, any of the systems may be used, but here the former indirect conversion system will be described. In recent years, commercialization of products of so-called multi-tube spherical apparatuses has advanced in which a plurality of pairs of X-ray tubes and X-ray detectors are mounted on a rotary ring, and development of peripheral techniques has advanced. The present invention can be applied to either a conventional mono-tube spherical apparatus or the multi-tube spherical apparatus. Here, mono-tube spherical type will be described.

FIRST EMBODIMENT

FIG. 1 is a diagram showing a constitution of the concentrated irradiation type radiotherapy apparatus according to a first embodiment of the present invention. The concentrated irradiation type radiotherapy apparatus includes a gantry 1100. The gantry 1100 includes a rotary ring 1102 held so as to be rotatable centering on a rotation center axis RA. An X-ray tube 1101 for generating a relatively high dose of radioactive rays for treatment is attached to the rotary ring 1102. A center axis (X-ray center axis) XC of an X-ray flux from the X-ray tube 1101 crosses at right angles to the rotation center axis RA. A multi-channeled X-ray detector 1103 is attached to the rotary ring 1102. The multi-channeled X-ray detector 1103 is disposed opposite to the X-ray tube 1101. The X-ray detector 1103 includes a single X-ray detection device array or a plurality of X-ray detection device arrays. One X-ray detection device array includes a plurality of X-ray detection devices arrayed along a circular arc centering on an X-ray focal point. The former is referred to as an X-ray detector for a single slice, and the latter is referred to as an X-ray detector for multi-slices or of an two-dimensional array type.

It is to be noted that the rotation center axis RA is assumed as a Z-axis, and a rotation coordinate system centering on the Z-axis is defined. In this case, the X-ray center axis XC is defined as a Y-axis, and an axis crossing at right angles to a ZY-axis is defined as an X-axis. This XYZ axes will appropriately be used in the following.

A multi-leaf collimator 1108 is disposed between the X-ray tube 1101 and the rotation center axis RA. In actual, the multi-leaf collimator 1108 is attached to an X-ray radiation window of the X-ray tube 1101. The multi-leaf collimator 1108 is a constituting device peculiar to the treatment apparatus, and is disposed so as to trim the X-ray radiated from the focal point of the X-ray tube 1101 in an arbitrary shape and size in an arbitrary position.

Figure 2A:
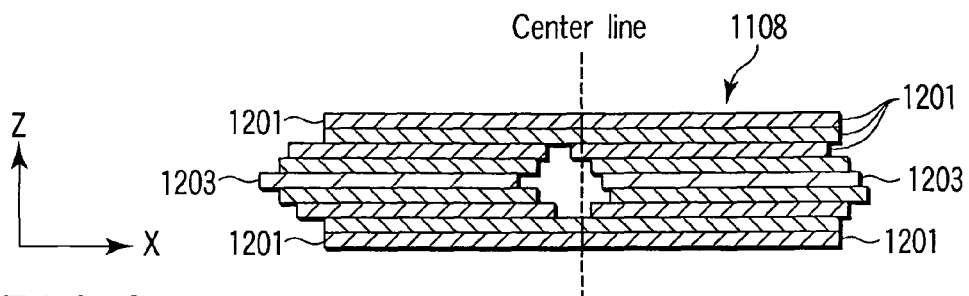
FIGS. 2A to 2D are diagrams showing a structure of a multi-leaf collimator of FIG. 1.

As shown in FIG. 2A, the multi-leaf collimator 1108 includes a plurality of leaves 1201, 1203. Each of the leaves 1201, 1203 has a strip shape having a width of 1 mm in a converted value on the rotation center axis RA. The respective leaves 1201, 1203 are disposed so as to be individually movable forwards/backwards in parallel with the X-axis. The plurality of leaves 1201, 1203 are arranged along the Z-axis. The leaves 1201, 1203 disposed adjacent to each other with respect to the X-axis constitute a pair. In FIG. 2A, nine pairs are shown.

Figure 2B:
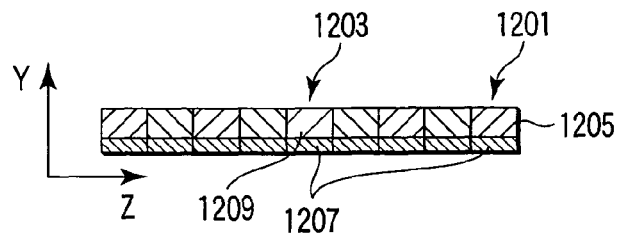
Figure 2C:
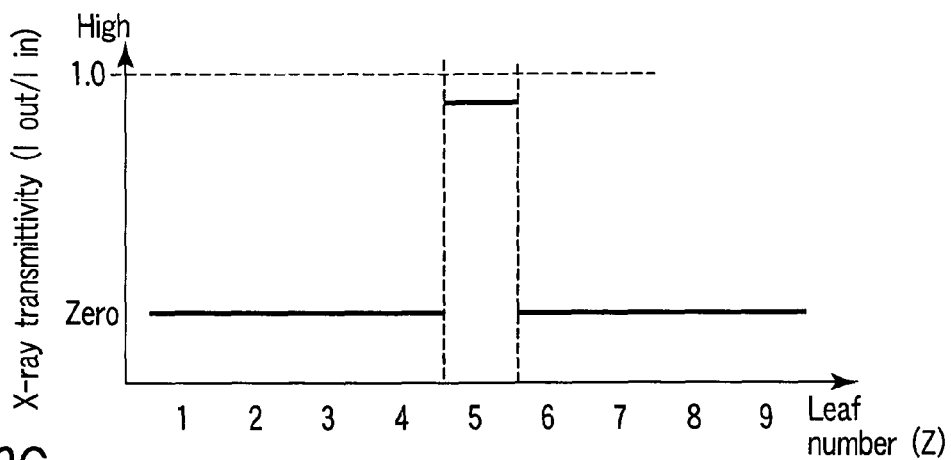
Figure 2D:
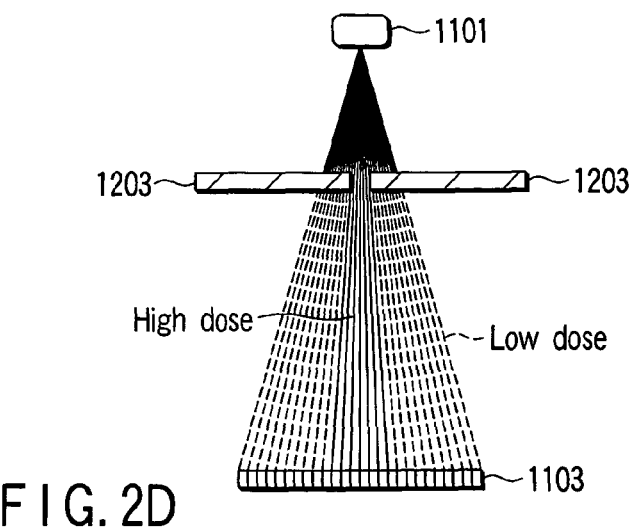

At least one pair of leaves 1203 in a middle with respect to the Z-axis are different in X-ray transmittivity from four pairs of other leaves 1201 disposed on each of opposite sides as shown in FIG. 2C. The X-ray transmittivity is defined as a ratio (Iout/Iin) of a dose Iout of transmitted X-rays to a dose Iin of incident X-rays. The leaves 1201 on the opposite sides have an X-ray transmittivity indicating zero or an approximate value. The leaves 1201 on the opposite sides substantially block off the X-rays. On the other hand, the middle leaves 1203 has an X-ray transmittivity which is higher than that of the leaves 1201 on the opposite sides and at which the rays are not passed without any attenuation, that is, which exceeds zero and is less than 1.0. Therefore, as shown in FIG. 2D, two middle leaves 1203 do not completely block off the X-rays, and have a function of leaking the X-rays attenuated to a low dose in accordance with the X-ray transmittivity and the dose of the incident X-rays. The X-ray transmittivity of the two middle leaves 1203 is set such that the dose of the leak X-rays satisfies safe standards at an imaging time and substantially agrees with a general dose at the imaging time.

As shown in FIG. 2B, the leaves 1201 on the opposite sides include a structure in which a shield plate 1205 formed of a material, such as lead, high in an attenuation coefficient and having a thickness necessary for obtaining the X-ray transmittivity of zero or the approximate value is bonded, for example, to an iron plate 1207 for compensating for rigidity. On the other hand, the middle leaves 1203 include a structure in which plate (diffusion plate) 1209 formed of a material such as Mo lower than lead in the attenuation coefficient is bonded to the same iron plate 1207. For a common movement mechanism, preferably the diffusion plate 1209 of the leaf 1203 is set to have the same thickness as that of the shield plate 1205 of the leaf 1201.

Figure 3A:
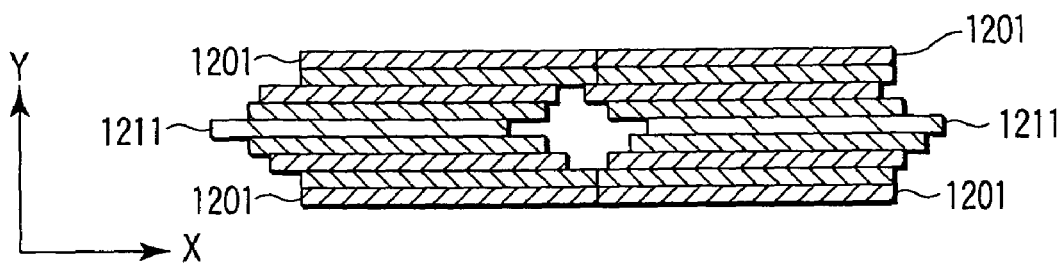
FIGS. 3A, 3B are diagrams showing a first modification example of the multi-leaf collimator.
Figure 3B:
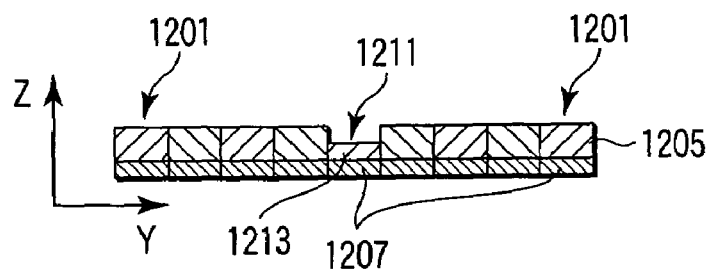

It is to be noted that the diffusion plate 1209 and shield plate 1205 do not have to be constituted of different metals. For example, the respective plates may be constituted of a lead-containing alloy, and a composition ratio of lead of the diffusion plate 1209 may be set to be lower than that of the shield plate 1205 to realize the above-described X-ray transmittivity relation between the leaves 1201 and 1203. Alternatively, as shown in FIGS. 3A, 3B, the shield plate 1205 is, for example, a lead plate, and a diffusion plate 1213 of the leaf 1203 is also the lead plate of the same material, the diffusion plate 1213 of the leaf 1203 is constituted to be thinner than the shield plate 1205, and the X-ray transmittivity relation between the leaves 1201 and 1203 may accordingly be realized.

Figure 4:
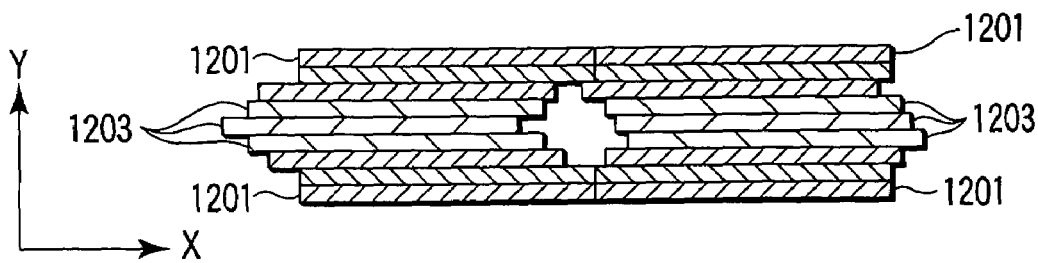
FIG. 4 is a diagram showing a second modification example of the multi-leaf collimator of FIG. 1.

In the above, the leaves 1203 having the high X-ray transmittivity constitute one middle pair, but as shown in FIG. 4, a plurality of middle leaves on each opposite side, three leaves here, that is, a plurality of middle pairs, three pairs may also be constituted of the leaves 1203 having the high X-ray transmittivity.

Turn back to FIG. 1. The X-ray detector 1103 is connected to a data collection circuit 1104 generally called a data acquisition system (DAS). The data collection circuit 1104 includes a function of converting an output (current signal) of each channel of the X-ray detector 1103 to a voltage signal, amplifying the signal, and converting the signal to a digital signal. The DAS 1104 is connected to a pre-processor 1106 for correcting non-uniformity between channels of DAS outputs via a noncontact type data transfer unit 1105 in which light and magnetism are mediums. Pre-processed data (projection data) is stored in an auxiliary storing unit 1112.

The auxiliary storing unit 1112 is connected to a system controller 1111 via a data/control bus. The system controller 1111 is connected to an image reconstructing unit 1114, display unit 1116, input device 1115, treatment planning system 1113, and treatment/scan controller 1110 via the data/control bus. The image reconstructing unit 1114 reconstructs image data from the projection data. The input device 1115 includes pointing devices such as a mouse, a keyboard, and an X-ray irradiation emergency stop button. The treatment planning system 1113 calculates an internal dose distribution of radioactive rays based on X-ray output dose characteristic data and tomographic image data. The treatment planning system 1113 calculates a relation between an aperture of the multi-leaf collimator 1108 and an X-ray tube rotation angle with respect to the region to be treated set via the input device 1115. The treatment planning system 1113 includes another support function exclusive for the treatment in order to carry out optimal irradiation. The treatment/scan controller 1110 controls the gantry 1100 and a high voltage generator 1109 in order to provide treatment following a treatment plan set by the treatment planning system 1113.

Figure 5:
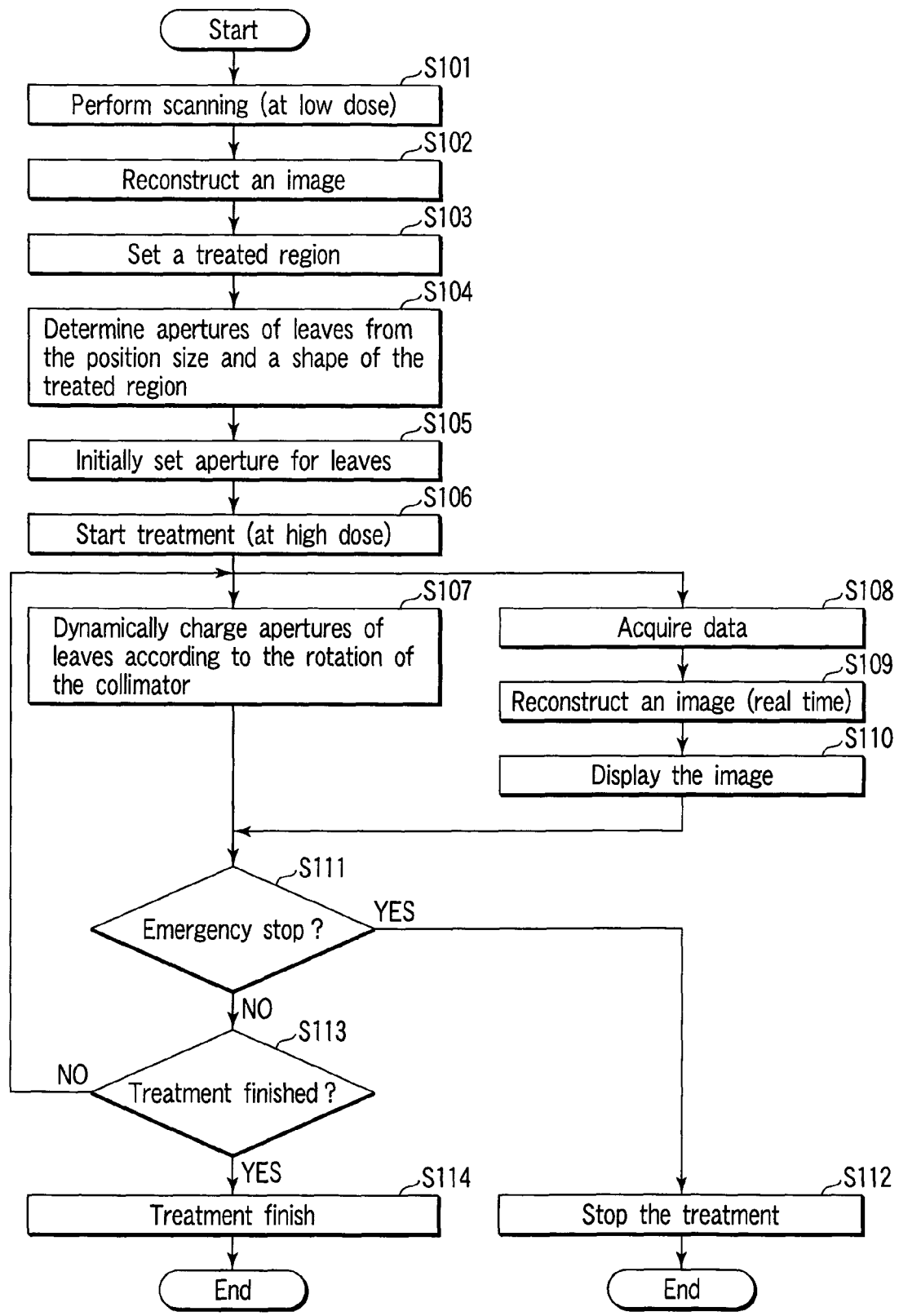
FIG. 5 is a flowchart showing a series of flows from when treatment is planned until the treatment ends in the first embodiment.

FIG. 5 shows a flow of a series of operations required for the treatment of the first embodiment. Before the treatment, first the scanning is performed under the control of the treatment/scan controller 1110 (S101). The scanning is an operation for acquiring internal tomographic image data of the subject, and is most different from the treatment in that the dose of the X-rays generated from the X-ray tube 1101 is low. Therefore, the treatment/scan controller 1110 supplies a control signal corresponding to relatively low tube voltage and current to the high voltage generator 1109. The treatment/scan controller 1110 supplies a control signal necessary for completely releasing the middle leaves 1203 with a maximum aperture with respect to a multi-leaf collimator driving unit 110, and completely closing the other leaves 1201. In this state, the rotary ring 1102 is continuously rotated, the X-rays are continuously or intermittently radiated, and transmitted X-rays are repeatedly detected at a predetermined sampling frequency by the detector 1103.

Figure 6:
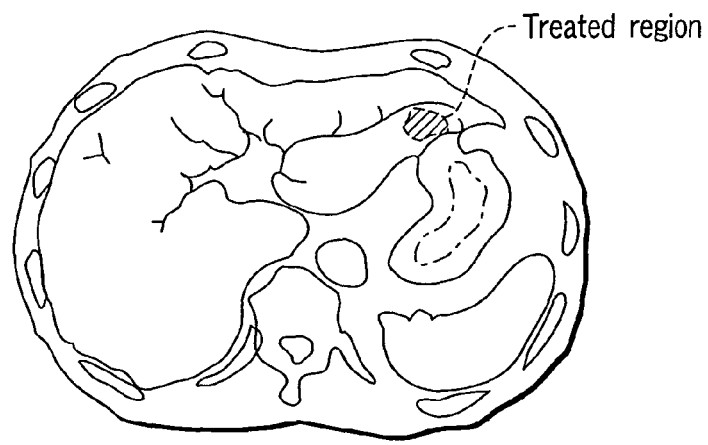
FIG. 6 is a diagram showing an image example displayed in S103 of FIG. 5;.
Figures 7A, 7B:
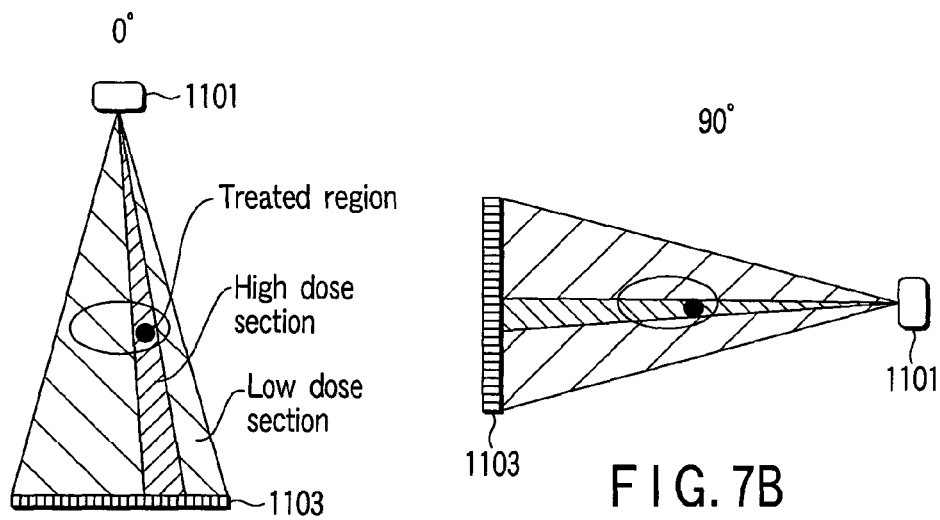
FIGS. 7A to 7D are supplementary explanatory views of an aperture control of S107 of FIG. 5.
Figures 7C, 7D:
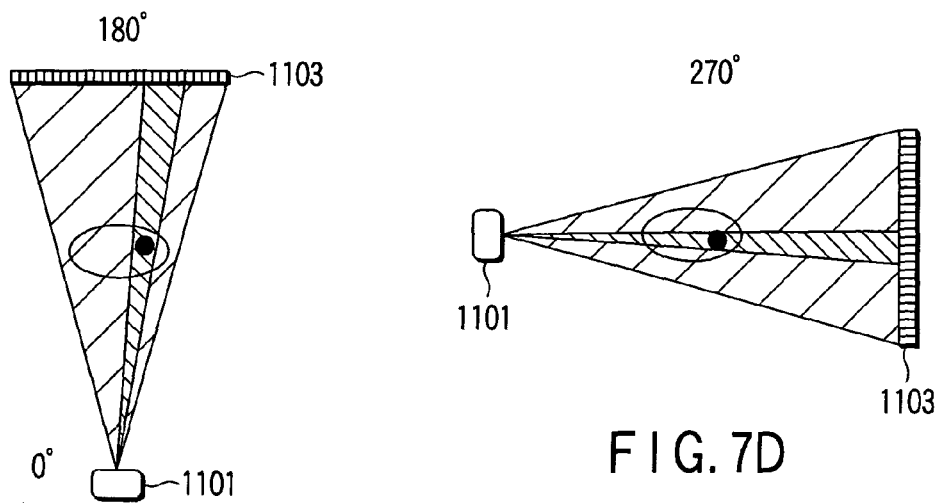

The tomographic image data is reconstructed based on the projection data collected by the scanning by the image reconstructing unit 1114 (S102). The tomographic image is displayed in the display unit 1116. FIG. 6 shows an example of the displayed tomographic image. On the image, an outer form of a region to be treated is traced by the operation of the input device 1115 by an operator. Accordingly, the region to be treated shown by slant lines is set (S103).

Based on a position, size, and shape of the set region to be treated, the treatment planning system 1113 calculates the apertures of the respective leaves 1201, 1203 of the multi-leaf collimator 1108 for each micro rotation angle of the X-ray tube 1101 (S104). It is to be noted that the apertures of the leaves 1201, 1203 are defined as movement distances from a center line. When the apertures of the leaves 1201, 1203 are individually set, the apertures can be set in accordance with the outer shape of the region to be treated.

With these operations, although not shown, the setting of irradiation conditions at a treatment time is completed, and the apertures of the respective leaves 1201, 1203 are initially set (S105). Thereafter, the treatment is started at an arbitrary time (S106). The treatment/scan controller 1110 supplies the control signal corresponding to relatively high tube voltage and current for exposure to the X-rays with a relatively high dose for the treatment. In this state, the rotary ring 1102 is continuously rotated, the X-rays are continuously radiated with the high dose for the treatment, and the apertures of the respective leaves 1201, 1203 calculated beforehand are dynamically changed in accordance with the rotation angle of the X-ray tube 1101 (S107). Accordingly, as shown in FIGS. 7A, 7B, 7C, 7D, in a rotation period, the region to be treated is constantly irradiated with the X-rays trimmed in a thin shape in accordance with the outer shape of the region to be treated by the aperture of the collimator 1108 in the form of beams with the high dose.

In the treatment period, the X-rays having the high dose and radiated from the X-ray tube 1101 pass through the aperture of the collimator 1108 as such without being attenuated. Moreover, the rays are attenuated and transmitted through the leaves 1203 whose middle X-ray transmittivity is not zero. The subject is irradiated with X-rays obtaining the low dose by the attenuation and together with the X-rays having the high dose for the treatment, and the X-rays transmitted through the subject are detected by the X-ray detector 1103. Accordingly, the projection data is collected (S108). It is to be noted that the subject is irradiated with the X-rays with the high dose via the aperture of the multi-leaf collimator 1108, and the X-rays attenuated and transmitted through the subject similarly obtain a relatively high dose. On the other hand, the subject is irradiated with the X-rays having the low dose via the middle leaves 1203 of the multi-leaf collimator 1108, and the X-rays are attenuated and transmitted through the subject to have the relatively low dose. Here, dynamic ranges of the detector 1103 and DAS 1104 are set on the basis of the X-rays with the low dose in the same manner as in the scanning. Therefore, the relatively high dose of X-rays saturates the dynamic range, and is detected as a maximum value of the range.

The image reconstructing unit 1114 reconstructs the tomographic image data based on a set of the projection data for $+\alpha$ (S109). This reconstruction process is a real time process. That is, the image reconstructing unit 1114 reconstructs the tomographic image data substantially in real time in parallel with generation of the radioactive rays for the treatment. The reconstructed tomographic image data is immediately displayed in the display unit 1116 (S110). This reconstruction and display process is continuously repeated in a period which is a time required for rotating an angle range of $180°+\alpha$ during the treatment, and accordingly a sectional mode including the region to be treated is imaged in the form of a dynamic image.

Figure 8:
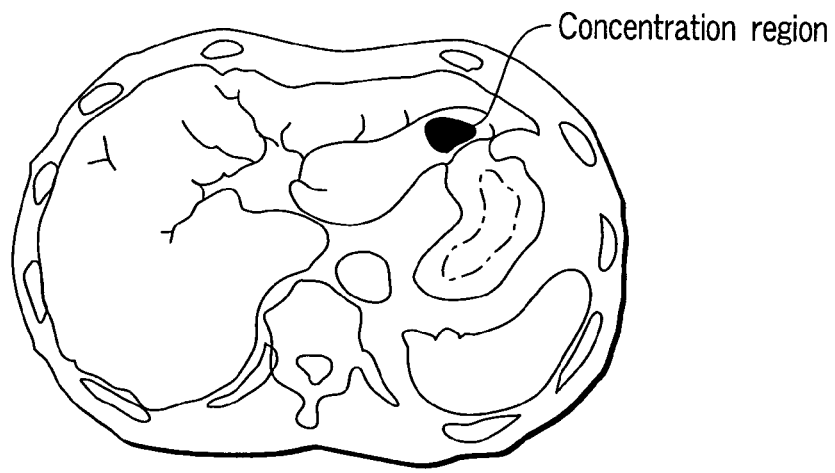
FIG. 8 is a diagram showing an image example displayed in S110 of FIG. 5.

FIG. 8 shows an example of the displayed tomographic image. As described above, the X-rays radiated via the aperture of the multi-leaf collimator 1108 have the high dose, and the dose is therefore detected as the maximum value of the dynamic range of the X-ray detector 1103 and data collection circuit 1104. Therefore, a region (concentration region) on which the X-rays are concentrated with the rotation is imaged at a maximum density. On the other hand, the X-rays radiated via the middle leaves 1203 of the multi-leaf collimator 1108 have the low dose, the dynamic ranges of the detector 1103 and DAS 1104 are effectively used, and an organization form in which differences of an X-ray absorption factor are reflected can be imaged. The operator recognizes a part indicating the maximum density as the region (concentration region) on which the X-rays are concentrated. Together with the region, the organization form of a region other than the concentration region can be observed.

Figure 9:
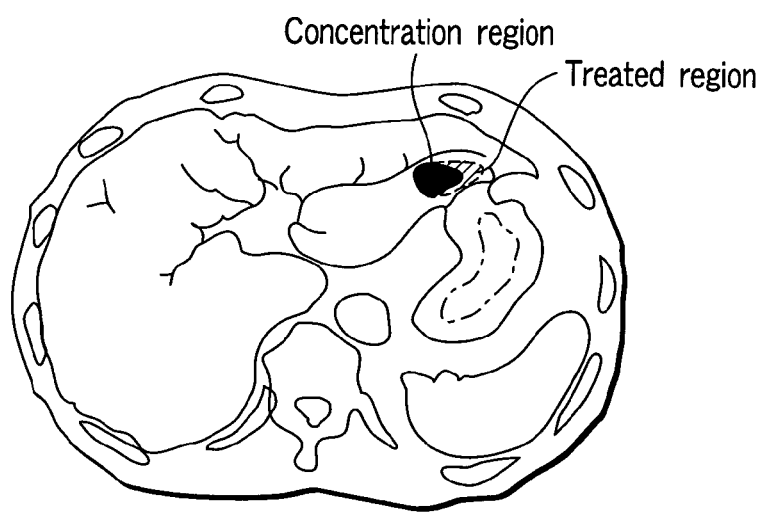
FIG. 9 is a diagram showing an image example at a time when the positional deviation displayed in S110 of FIG. 5 is caused.

Here, in the treatment period, the concentration region sometimes deviates from the region to be treated because of body movement of the subject. FIG. 9 shows an example of the tomographic image for this case. The concentration region is display in black at a high density. Moreover, it can be observed that the image of the region to be treated deviates from the concentration region and is reflected. From this image, the operator confirms a degree of the positional deviation of the region to be treated with respect to the concentration region, and presses an irradiation emergency stop button of the input device 1115. Following the operation of this irradiation emergency stop button, the treatment/scan controller 1110 recognizes that an emergency stop command has been inputted (S111), and a measure necessary for stopping the irradiation of the subject with the X-rays in emergency is taken (S112). In general, the application of the tube voltage to the X-ray tube 1101 from the high voltage generator 1109 and the supply of the tube current are stopped in emergency. However, when the X-ray tube 1101 includes a shutter device instead of or together with the stopping of the application of the tube voltage and the supply of the tube current, a shutter may be closed to handle the emergency stop.

It is to be noted that even when the position of the region to be treated deviates from the concentration region, and when the positional deviation is subtle, or when the positional deviation is solved and there is a tendency of returning to an original position, the treatment is preferably continued as such without stopping in emergency. In this case, the operator substantially designates a center position of the region to be treated which deviates from the concentration region having the high density and which can partially visually be recognized on the tomographic image. Accordingly, the apertures of the leaves 1201, 1203 are immediately recalculated by the treatment planning system 1113, and the process can be switched to an aperture control in accordance with the calculation result.

When the positional deviation of the region to be treated with respect to the concentration region is not caused or is subtle on the tomographic image, the emergency stop command is not inputted. The process of S107 to S111 is repeated until a treatment finish condition is satisfied in S113. When the treatment finish condition is satisfied in S113, the treatment is finished (S114).

In this manner, according to the present embodiment, the region to be treated is displayed as a form image together with a peripheral organization in the treatment period. Moreover, since the irradiation concentration region is displayed in the high density on the image, the positional deviation between the region and image is immediately monitored, and the emergency stop can be made if necessary. Therefore, safety at a treatment time can be enhanced.

Figure 10A:
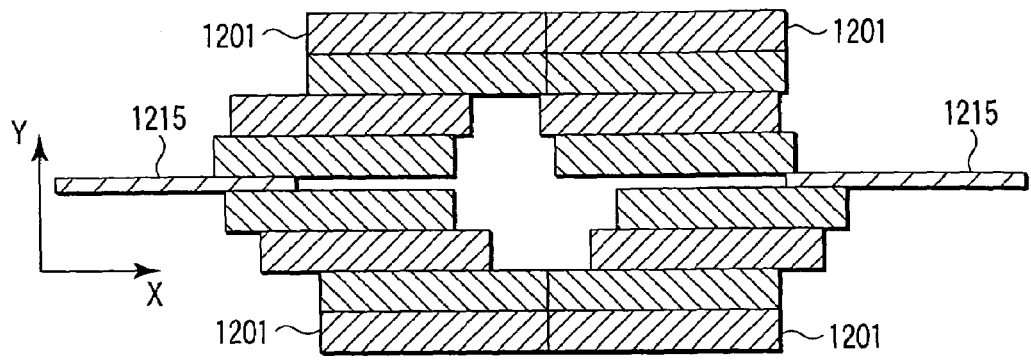
FIGS. 10A, 10B are diagrams showing a third modification example of the multi-leaf collimator of FIG. 1.
Figure 10B:
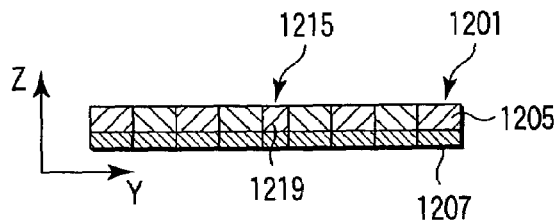

It is to be noted that in the above description, the middle leaves 1203 have an X-ray transmittivity higher than that of the other leaves 1201 among the leaves constituting the multi-leaf collimator 1108. This is for purposes of realizing of the form imaging to avoid the saturation of the dynamic range, and of reducing the exposure of the normal region other than the region to be treated. Similar purposes may also be realized by constituting the width of the middle leaf 1215 of the multi-leaf collimator 1108 to be smaller than that of another leaf 1201 as shown in FIGS. 10A, 10B. The widths of two middle leaves 1215 are determined based on the dose of X-rays for the treatment so that the dose of X-rays passed through a slit having this width avoids the saturation of the dynamic range, further satisfies a safety standard at the imaging time, and substantially agrees with a general dose at the imaging time.

A plate 1219 of the middle leaf 1215 is constituted of the same material as that of the shield plate 1205 of the other leaf 1201, such as lead, in the same thickness. In this constitution example, the middle leaf 1215 has an X-ray transmittivity of zero, equivalent to that of the other leaf 1201, that is, a shield property.

At the treatment time, the middle leaves 1215 are completely released. Since the width of the middle leaf 1215 is reduced, the X-ray shaped to be thin through the slit, passed through the subject, and incident upon the detector 1103 substantially has the low dose, and the dynamic ranges of the detector 1103 and DAS 1104 are not saturated. Accordingly, the imaging of the forms of the region to be treated and peripheral organization can be secured. When the image monitor is not required during the treatment, the apertures of the middle leaves 1215 are controlled in accordance with the region to be treated, and accordingly the unnecessary exposure can be avoided. Moreover, when the middle leaves 1215 are completely released to monitor the image during the treatment, a structure may be used in which the rotary ring 1102 is slanted with respect to the rotation center axis RA in order to reduce the exposure of the normal region.

Figure 11A:
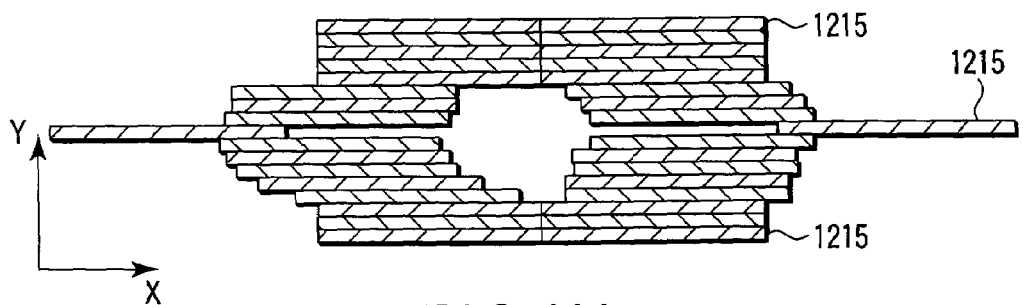
FIGS. 11A, 11B are diagrams showing a fourth modification example of the multi-leaf collimator of FIG. 1.
Figure 11B:
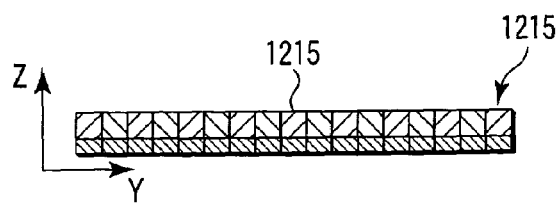

This constitution example can be developed as shown in FIGS. 11A, 11B. That is, all the leaves constituting the multi-leaf collimator 1108 may be constituted of the middle leaves 1215 having the same small width. In this case, the collimator aperture can be approximated by the outer shape of a non-treated region.

SECOND EMBODIMENT

Figure 12:
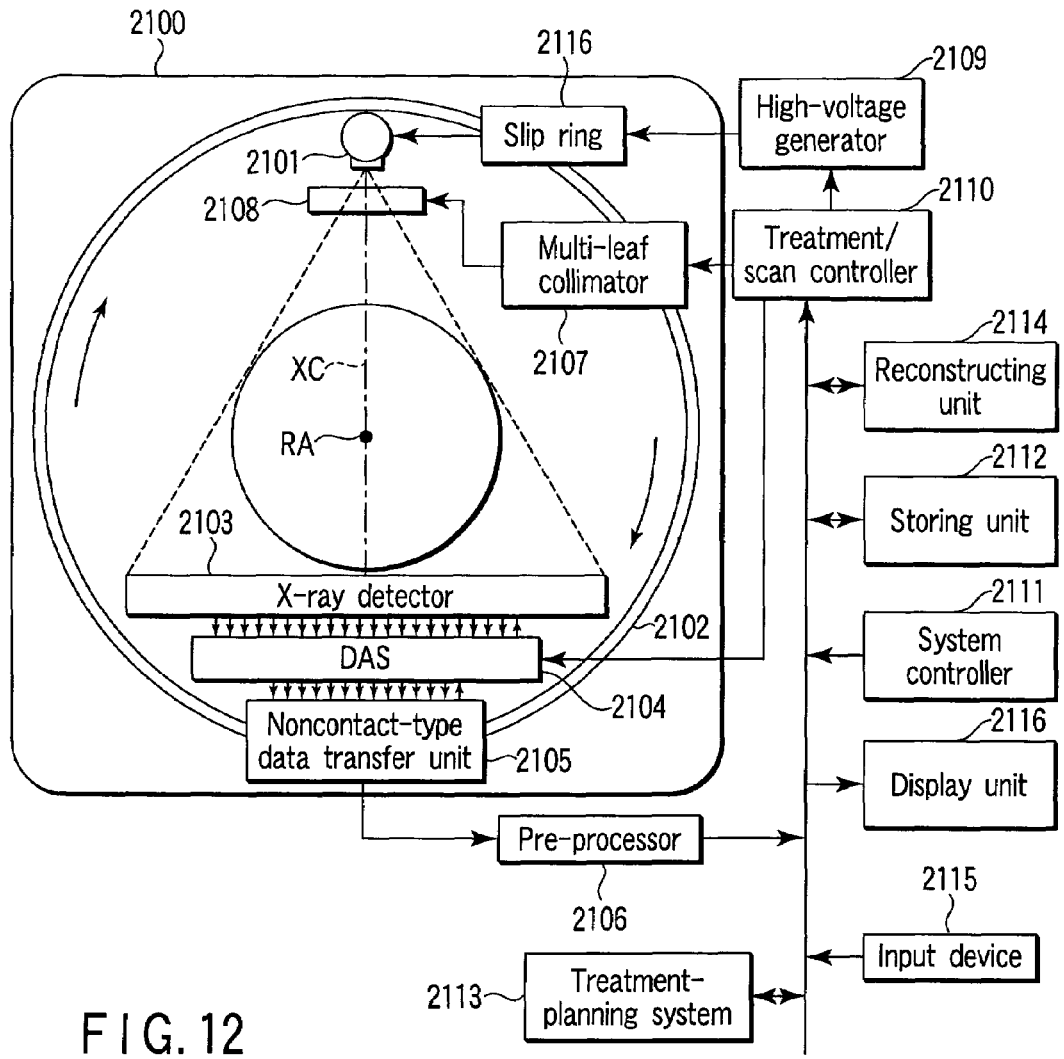
FIG. 12 is a diagram showing the constitution of the concentrated irradiation type radiotherapy apparatus according to a second embodiment of the present invention.

FIG. 12 is a diagram showing the constitution of the concentrated irradiation type radiotherapy apparatus according to a second embodiment of the present invention. The concentrated irradiation type radiotherapy apparatus includes a gantry 2100. The gantry 2100 includes a rotary ring 2102 held so as to be rotatable centering on the rotation center axis RA. An X-ray tube 2101 for generating the relatively high dose of radioactive rays for the treatment is attached to the rotary ring 2102 opposite to the rotation center axis RA, that is, in a position where the center axis (X-ray center axis) XC of the X-ray flux from the X-ray tube 2101 crosses at right angles to the rotation center axis RA. A multi-channeled X-ray detector 2103 is attached to a position opposite to the X-ray tube 2101 via the rotation center axis RA on the rotary ring 2102. The multi-channeled X-ray detector 2103 includes a plurality of X-ray detection devices arrayed in a direction substantially crossing at right angles to the rotation center axis RA and X-ray center axis XC, in actual along the circular arc centering on the X-ray focal point. The X-ray detector 2103 includes the single X-ray detection device array or a plurality of X-ray detection device arrays. The former is referred to as the X-ray detector for the single slice, and the latter is referred to as the X-ray detector for multi-slices or of the two-dimensional array type.

It is to be noted that the rotation center axis RA is assumed as the Z-axis, and the rotation coordinate system centering on the Z-axis is defined by an XY coordinate system. In this case, the X-ray center axis XC is defined as the Y-axis, and the axis crossing at right angles to the ZY-axis is defined as the X-axis. The XYZ axes will appropriately be used in the following.

A movable multi-leaf collimator 2108 is disposed between the X-ray tube 2101 and the rotation center axis RA. In actual, the multi-leaf collimator 2108 is attached to the X-ray radiation window of the X-ray tube 2101. The multi-leaf collimator 2108 is the constituting device peculiar to the treatment apparatus, and is disposed so as to trim the X-ray radiated from the focal point of the X-ray tube 2101 in the arbitrary shape and size in the arbitrary position.

Figure 13:
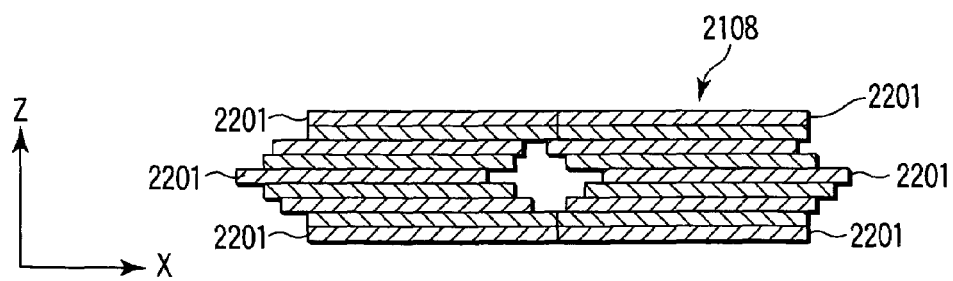
FIG. 13 is a diagram showing the structure of the multi-leaf collimator of FIG. 12.

As shown in FIG. 13, the multi-leaf collimator 2108 includes a plurality of leaves 2201 each of which is disposed to be movable forwards/backwards along the X-axis and each of which has a strip shape having a width of 1 mm in the converted value on the rotation center axis RA. In actual, assuming that the X-ray center axis XC is the center line, two leaves 2201 constitute a pair so as to open on either side via the center line. A plurality of leaf pairs, nine pairs here are juxtaposed.

The X-ray detector 2103 is connected to a data collection circuit 2104 generally called the data acquisition system (DAS). The data collection circuit 2104 includes a function of converting the output (current signal) of each channel of the X-ray detector 2103 to the voltage signal, amplifying the signal, and converting the signal to the digital signal. The DAS 2104 is connected to a pre-processor 2106 for correcting the non-uniformity between the channels of DAS outputs via a noncontact type data transfer unit 2105 in which the light and magnetism are mediums. The pre-processed data (projection data) is stored in an auxiliary storing unit 2112.

The auxiliary storing unit 2112 is connected to a system controller 2111 via the data/control bus. The system controller 2111 is connected to an image reconstructing unit 2114, display unit 2116, input device 2115, treatment planning system 2113, and treatment/scan controller 2110 via the data/control bus. The image reconstructing unit 2114 reconstructs the image data from the projection data. The input device 2115 includes the pointing devices such as the mouse, and the keyboard. The treatment planning system 2113 prepares a treatment plan. The treatment/scan controller 2110 controls the gantry 2100 and a high voltage generator 2109 in order to provide the treatment following the treatment plan.

The treatment planning system 2113 includes a function of calculating the internal dose distribution of radioactive rays based on the X-ray output dose characteristic data and tomographic image data. The treatment planning system 2113 includes a function of calculating the relation between the aperture of the multi-leaf collimator 2108 and an X-ray tube rotation angle with respect to the region to be treated set via the input device 2115. Furthermore, the treatment planning system 2113 includes a function peculiar to the present embodiment concerning the realization of the treatment efficiency and exposure reduction in a compatible manner.

In the present embodiment, to realize both the treatment efficiency and exposure reduction in the compatible manner, the irradiation of the subject with the X-rays is suspended in a part of a period in which the X-ray tube 2101 rotates once around the subject. The treatment planning system 2113 includes a function of determining the part of the rotation period corresponding to the suspension of the irradiation with the X-rays (this part of the period will hereinafter be referred to as an irradiation suspension period, X-ray non-irradiation period, or irradiation limit period). This function will be described hereinafter.

Figure 14:
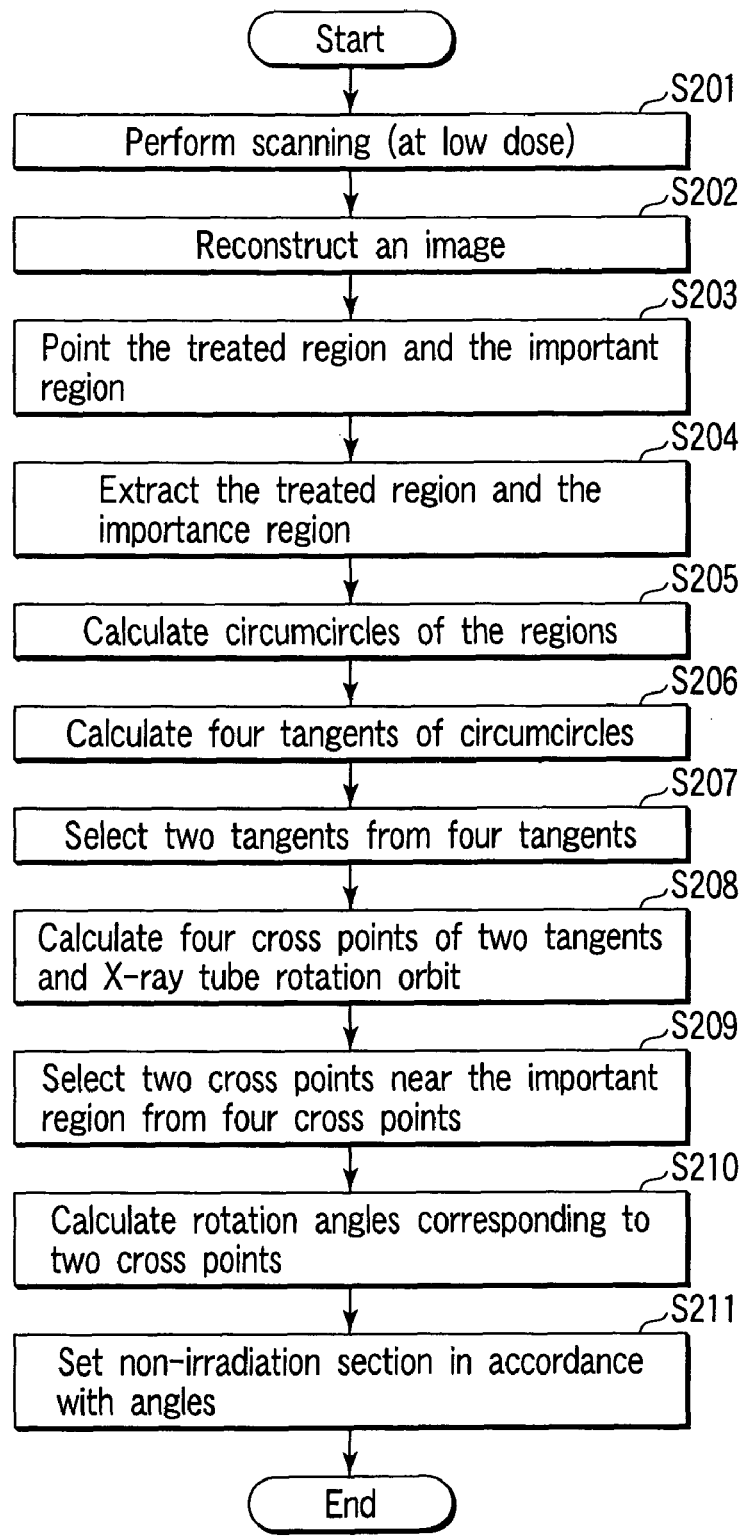
FIG. 14 is a flowchart showing a procedure for setting an X-ray non-irradiation section by a treatment planning system of FIG. 12.

FIG. 14 shows a procedure for determining the X-ray non-irradiation period. First, the subject is scanned with the relatively low dose, and the projection data, for example, for $180°+\alpha°$, necessary for reconstructing the tomographic image data is collected (S201). In the image reconstructing unit 2114, the tomographic image data is reconstructed based on the collected projection data (S202), and displayed in the display unit 2116. It is to be noted that the displayed image center agrees with an original point of a display coordinate system, and corresponds to the rotation center axis RA.

Figure 15:
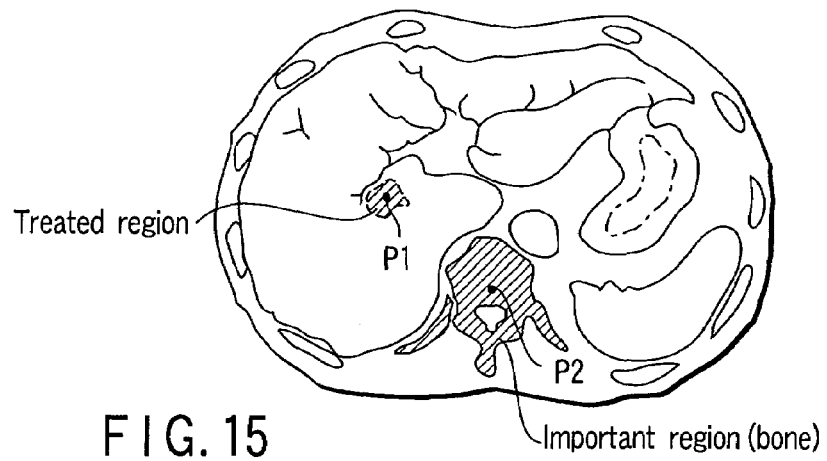
FIG. 15 is a diagram showing a display image example corresponding to S203 of FIG. 14.

As shown in FIG. 15, the operator (surgery operator) designates one point P1 on the region to be treated on the displayed tomographic image via the input device 2115, and further designates one point P2 on an important region (S203). It is to be noted that a plurality of points may be designated with respect to a plurality of important region. The important region has a relatively high X-ray sensitivity (X-ray absorption factor), and is a region relatively highly influenced by the exposure to the X-ray irradiation, and typical examples of the region include bone, glandular system, and testicle.

In the present embodiment, when direct irradiation of the important region with the X-rays is limited, the exposure reduction with respect to the important region is realized. When the direct irradiation with the X-rays is limited, an effect of inhibiting drop of the treatment efficiency is acquired simultaneously with the exposure reduction with respect to the important region. That is, during the treatment, the X-ray tube 2101 moves along a circumferential orbit. On the orbit, the important region is disposed between the X-ray tube 2101 and the region to be treated, and there exists a partial section where the region to be treated entirely or partially hides behind an X-ray shade of the important region.

In this partial section, the region to be treated is irradiated with the X-rays largely attenuated by the important region. Therefore, a ratio of the dose of X-rays actually reaching the region to be treated to the irradiation dose of a patient with the X-rays, that is, the treatment efficiency drops. When the irradiation with the X-rays is limited in the partial section, the drop of the treatment efficiency can be avoided.

The treatment planning system 2113 enlarges and searches peripheral pixels from one point P1 designated on the region to be treated of the image, which is a start point, and applies a threshold value process with respect to CT values, or existing region extraction processes such as a differential value process to extract the region to be treated (S204). Similarly the treatment planning system 2113 extracts the important region from one point P2 designated on the important region of the image, which is the start point.

Figure 16:
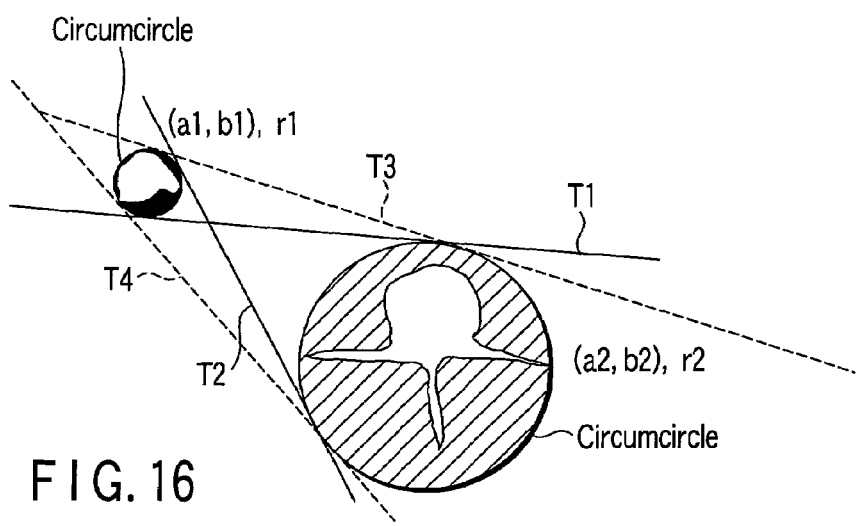
FIG. 16 is a supplementary diagram of S205 to S207 of FIG. 14.

Next, as shown in FIG. 16, a circle circumscribed in the extracted region to be treated (circumcircle) is calculated by the treatment planning system 2113 (S205). Similarly, a circle circumscribed in the extracted important region (circumcircle) is calculated by the treatment planning system 2113. The treatment planning system 2113 calculates the apparatuses of the respective leaves 2201 of the multi-leaf collimator 2108 for each micro rotation angle of the X-ray tube 2101 based on a radius and position of the circumcircle of the region to be treated. It is to be noted that the aperture of the leaf 2201 is defined as the movement distance from the center line of the collimator 2108. When the aperture of each leaf 2201 is set for each rotation angle, the X-ray is aligned with the region to be treated in each position of a moving orbit of the X-ray tube 2101, and the irradiation concentrated on the region to be treated can be realized.

Next, the treatment planning system 2113 calculates four tangents T1, T2, T3, T4 which contact both the circumcircles of the region to be treated and important region (S206). A method for calculating the tangents contacting two circles is known, and the tangents can be obtained by solving the following simultaneous equations. It is to be noted that it is assumed that the center position of the circumcircle of the region to be treated is (a1, b1), a radius of the circumcircle of the region to be treated is r1, the center position of the circumcircle of the important region is (a2, b2), and the radius of the circumcircle of the important region is r2. It is also assumed that an inclination of the obtained tangent is m and a cut piece is $\beta$.

$(m \cdot a1 - b1 + \beta)^2 = r1 \cdot (1+m)$ $(m \cdot a2 - b2 + \beta)^2 = r2 \cdot (1+m)$ From the four tangents T1, T2, T3, T4 calculated in S206, the treatment planning system 2113 selects two tangents T1, T2 which intersect with each other between the circumcircles of the region to be treated and the important region, or between the designated points P1 and P2 on the region to be treated and the important region (S207). As understood from FIG. 17, one tangent T1 indicates a boundary line via which the region to be treated starts entering the X-ray shade of the important region, and the other tangent T2 indicates a boundary line via which the region to be treated completely leaves the X-ray shade of the important region.

Moreover, four points CP1, CP2, CP3, CP4 are calculated in which the selected two tangents T1, T2 intersect with a rotation orbit of the X-ray tube 2101 (S208). Two points CP1, CP2 closest to the center position of the important region are selected from four points CP1, CP2, CP3, CP4 (S209). The original points of two selected points CP1, CP2, that is, the angles around the rotation center axis RA are calculated (S210). For example, the rotation angle of the intersection CP1 is calculated as 95°, and that of the intersection CP2 is calculated as 145°. The treatment planning system 2113 sets the calculated angle range of 95° to 145° as an X-ray non-irradiation section or X-ray limit section (S211).

Figure 18:
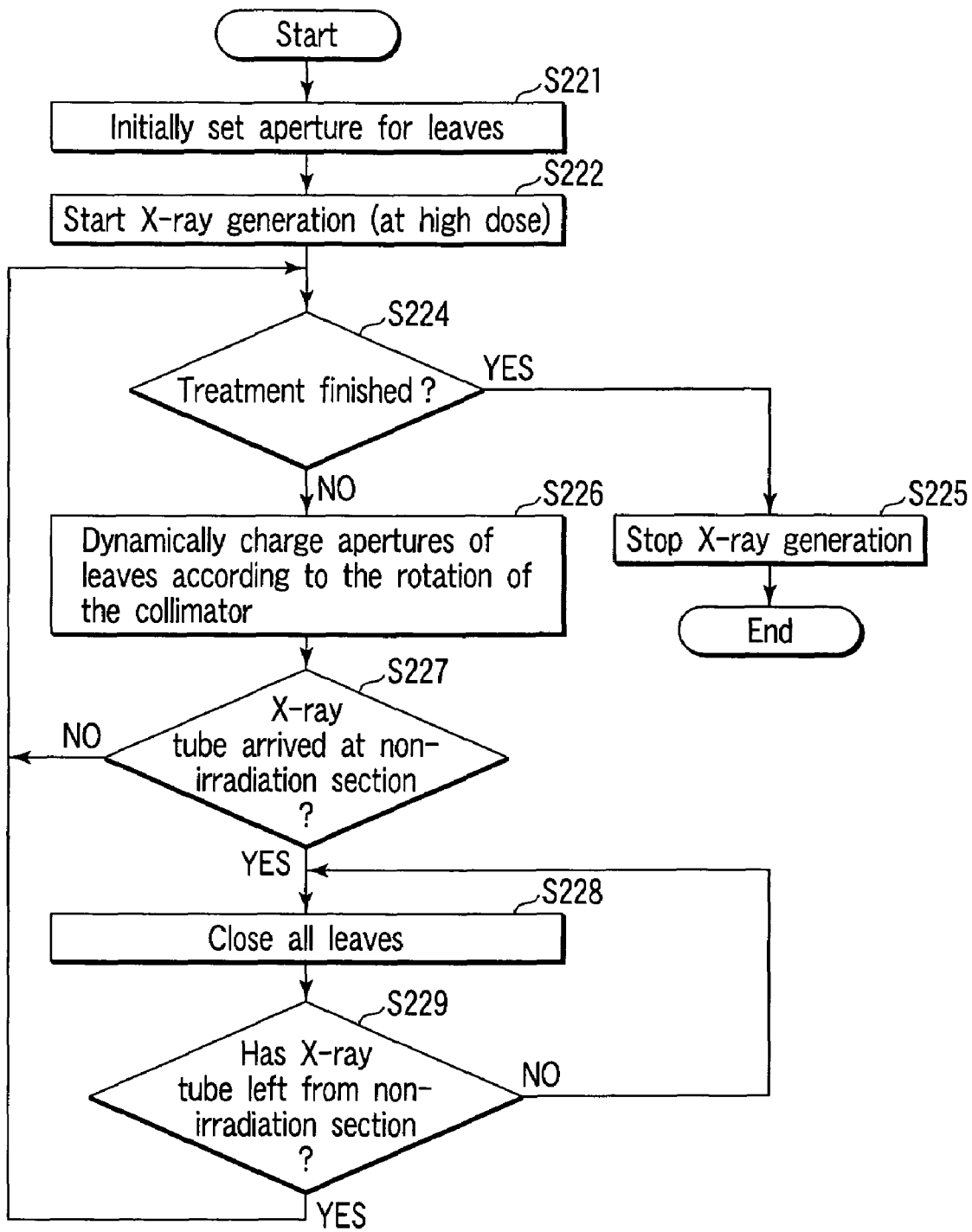
FIG. 18 is a flowchart showing a treatment operation procedure under a treatment/scan controller of FIG. 12.
Figure 19A:
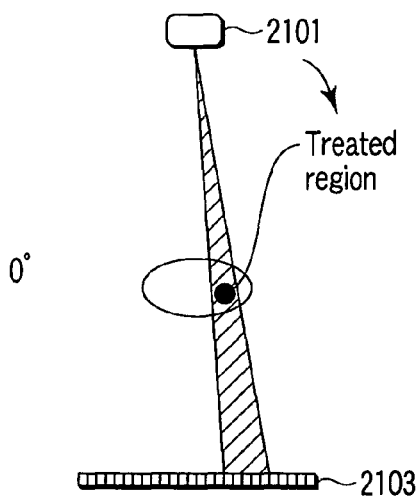
FIGS. 19A to 19D are supplementary diagrams of S226 of FIG. 18.
Figure 19B:
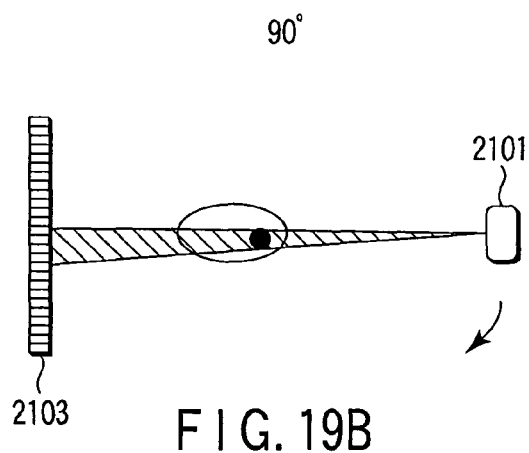
Figure 19C:
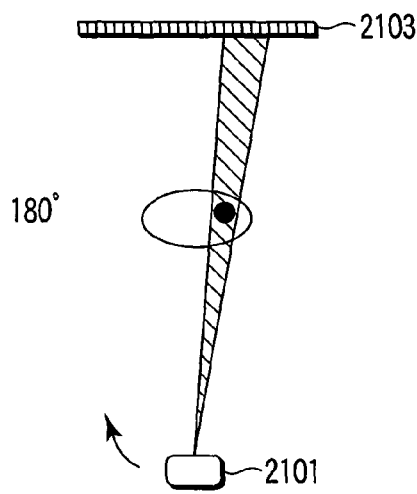
Figure 19D:
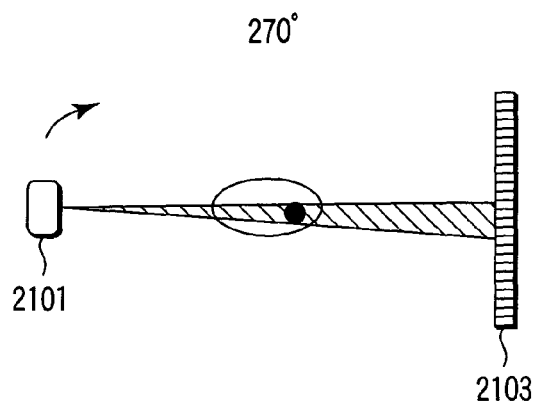

FIG. 18 shows a treatment operation procedure by the treatment/scan controller 2110. First, the treatment/scan controller 2110 sets the aperture of each leaf of the collimator 2108 to an initial state (S221). For example, when an irradiation start angle is 0°, the aperture of each leaf is set to that corresponding to the rotation angle 0°.

The treatment/scan controller 2110 supplies a trigger signal to a rotary ring driving unit (not shown). The rotary ring driving unit starts rotating the rotary ring 2102. The rotary ring driving unit maintains a rotation speed, when the rotation speed of the rotary ring 2102 reaches a predetermined speed. The treatment/scan controller 2110 supplies an X-ray generation control signal to the high voltage generator 2109, when the X-ray tube 2101 reaches an irradiation start angle of 0°. The X-ray generation control signal corresponds to the planned irradiation condition.

Accordingly, the tube voltage is applied between a cathode and anode to the X-ray tube 2101 from the high voltage generator 2109, a filament current is supplied, the tube current flows, and the X-rays are generated from the X-ray tube 2101 with the set dose and radiation quality (S222). The generation of the X-rays is continued until predetermined treatment finish condition is satisfied in a treatment plan stage in S224. When the predetermined finish condition is satisfied in the treatment plan stage, the treatment/scan controller 2110 supplies the control signal necessary for stopping the generation of X-rays from the X-ray tube 2101 to the high voltage generator 2109. Accordingly, the application of the tube voltage and the supply of the tube current to the X-ray tube 2101 from the high voltage generator 2109 are stopped to stop the generation of the X-rays (S225).

In the treatment period, the treatment planning system 2113 supplies the control signal to the multi-leaf collimator driving unit 2107 in accordance with the constantly changing rotation angle of the X-ray tube 2101 recognized by counting pulses from an angle sensor including a rotary encoder (not shown) to dynamically change the aperture of each leaf of the multi-leaf collimator 2108 (S226). Accordingly, as shown in FIGS. 19A, 19B, 19C, 19D, during the rotation period, the high dose of X-rays thinly trimmed in a shape in accordance with the circumcircle of the region to be treated in the form of beams by the aperture of the collimator 2108 are constantly aligned with the region to be treated, and concentrated treatment is realized.

Figure 20:
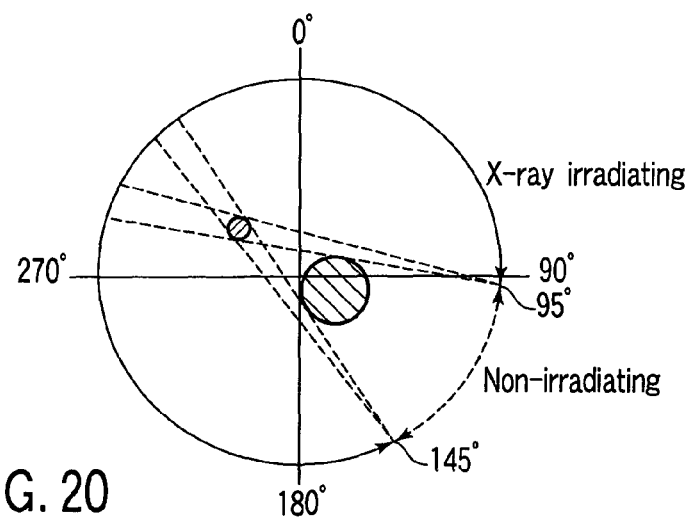
FIG. 20 is a diagram showing an X-ray non-irradiation period by the operation of S227 to S229 of FIG. 18 on a rotation orbit of an X-ray tube.

In the treatment period, as shown in FIG. 20, when the rotation angle of the X-ray tube 2101 reaches a preset start point of the non-irradiation section (95° corresponding to CP1) (S227), the treatment planning system 2113 controls the multi-leaf collimator driving unit 2107 to set the apertures of all the leaves 2201 of the collimator 2108 to zero, that is, to close all the leaves 2201 (S228). Since the leaf 2201 is formed of lead and include the shield property, all the leaves 2201 are closed to stop the irradiation of the region to be treated with the X-rays by a shutter effect.

It is to be noted that a shutter unit including two plates or a multiplicity of plates may be disposed between a patient and the X-ray tube 2101 such as between the X-ray tube 2101 and collimator 2108 to close the shutter instead of closing all the leaves 2201 of the multi-leaf collimator 2108. There is a possibility that the shutter can open/close more quickly than the leaves 2201 of the multi-leaf collimator 2108.

A state in which all the leaves 2201 of the multi-leaf collimator 2108 are closed is continued until the rotation angle of the X-ray tube 2101 reaches an end point (145° corresponding to CP2) of the preset non-irradiation section (S229). When the rotation angle of the X-ray tube 2101 reaches the end point (145°) of the preset non-irradiation section, all the leaves 2201 of the multi-leaf collimator 2108 are opened in the aperture in accordance with a rotation angle of 145°, and the irradiation of the region to be treated with the X-rays is resumed.

FIG. 21 shows changes of the rotation angle of the X-ray tube 2101 with an elapse of time. During the treatment, the X-ray tube 2101 repeatedly rotates along the rotation orbit between 0° and 360° many times. In this rotation period, the irradiation of the subject (patient) with the X-rays is limited in a partial period corresponding to a section where the X-ray tube 2101 moves to 145° from 95°.

It is to be noted that to "limit the X-ray irradiation" is defined as the drop of the irradiation dose into the patient as compared with a period in which X-ray irradiation is not limited. This includes the complete stopping of the X-ray irradiation as described above (the reducing of the irradiation dose onto the patient substantially to a zero value) and the reducing of the irradiation dose onto the patient to a zero approximate value to such an extent that the influence of the exposure is little.

In order to limit the X-ray irradiation in the partial period, in the above, all the leaves 2201 are closed. In order to limit the X-ray irradiation in the partial period, the generation of X-rays itself may also be suspended.

Figure 22:
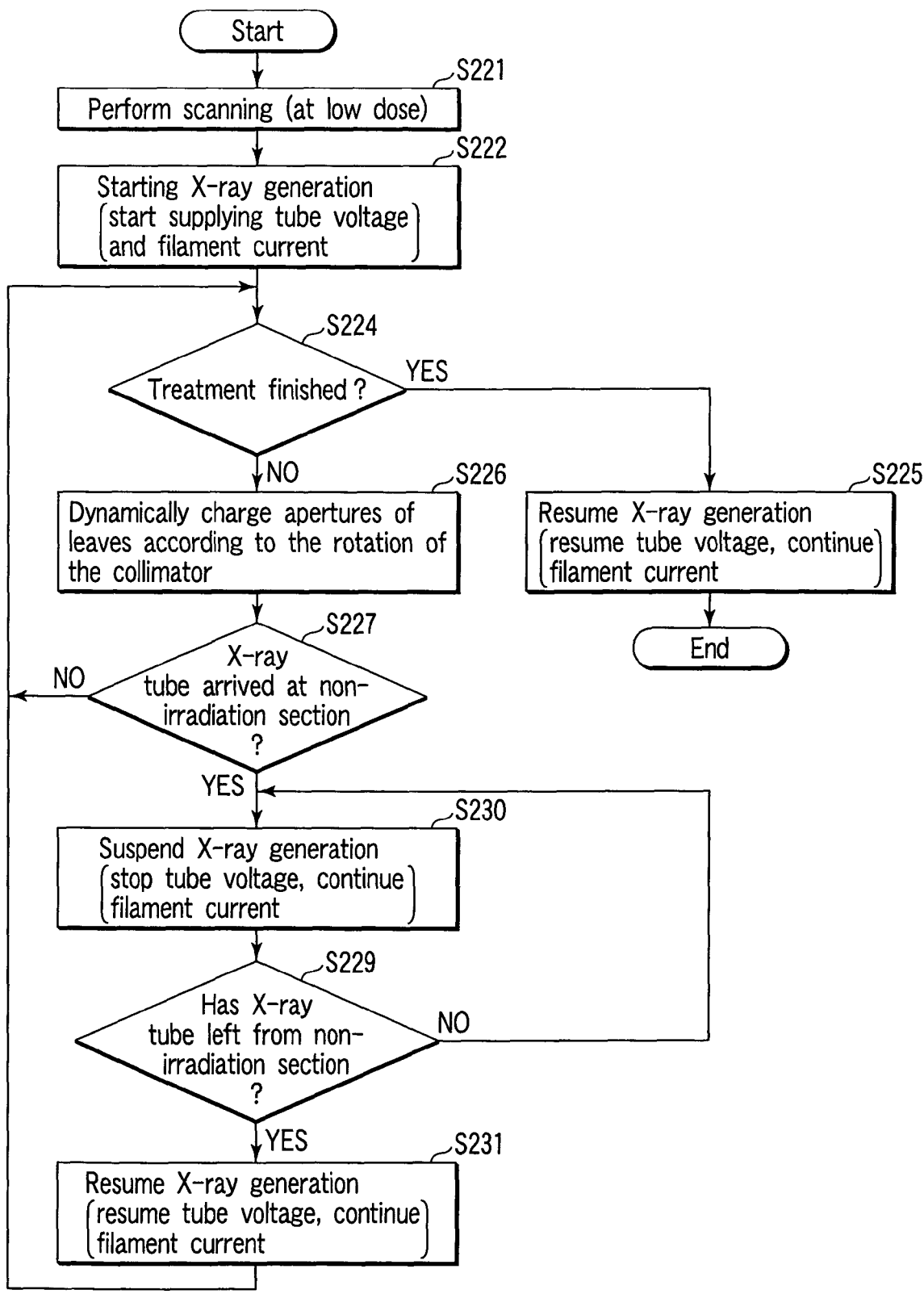
FIG. 22 is a flowchart showing another procedure for performing the treatment under the treatment/scan controller of FIG. 12.

FIG. 22 showing the operation. In FIG. 22, the same steps as those of FIG. 18 are denoted with the same reference numerals. When the X-ray tube 2101 reaches a start point (95° corresponding to CP1) of the non-irradiation section in S227, the treatment planning system 2113 supplies a control signal for temporarily suspending the generation of the X-rays from the X-ray tube 2101 to the high voltage generator 2109 (S230). Concretely, the controlled high voltage generator 2109 stops the application of the tube voltage, and continues the supply of the filament current. As well known, the filament current heats a filament, and the generation of thermoelectrons is accordingly promoted. During the suspension of the generation, when the supply of the filament current is continued, a temperature drop of the filament is avoided, and a high temperature state of the filament and the generation of the thermoelectrons are maintained. When the supply of the filament current is stopped, and even when the supply of the filament current is resumed, a delay time caused by the heating of the filament is generated until the generation is resumed. However, when the supply of the filament current is continued also during the suspension of the generation, the high temperature state of the filament can be maintained, the generation can accordingly immediately be resumed without any delay from the resuming of the application of the tube voltage.

A state in which the tube voltage application is stopped is continued until the rotation angle of the X-ray tube 2101 reaches the end point (145° corresponding to CP2) of the preset non-irradiation section (S229). When the rotation angle of the X-ray tube 2101 reaches the end point (145°) of the present non-irradiation section, the application of the tube voltage is resumed (S231), and the generation of X-rays and accordingly the irradiation of the region to be treated with the X-rays are resumed.

In this manner, according to the present embodiment, the important region enters between the X-ray tube 2101 and the region to be treated during the treatment, and the irradiation of the patient with the X-rays is suspended in a partial section or period in which the region to be treated enters the X-ray shade of the important region. Accordingly, the treatment efficiency in the region to be treated and the exposure reduction onto the important region can be achieved in the compatible manner.

It is to be noted that as described above, the X-ray irradiation is suspended in a section from the angle (e.g., 95°) of the boundary line T1 via which the region to be treated starts entering the X-ray shade of the important region to the angle (e.g., 145°) of the boundary line T2 via which the region to be treated completely leaves the X-ray shade of the important region. However, in a micro section from the angle (95°) of the boundary line T1 via which the region to be treated starts entering the X-ray shade of the important region until the region to be treated completely enters the X-ray shade of the important region, and in a micro section from when the region to be treated starts leaving the X-ray shade of the important region until the angle (145°) of the boundary line T2 via which the region to be treated completely leaves the X-ray shade of the important region, a fan angle of the X-rays can be controlled to partially irradiate the region to be treated with the X-rays. Therefore, when the region to be treated is even partially irradiated with the X-rays in these micro sections, the treatment efficiency can further be enhanced.

Figure 23:
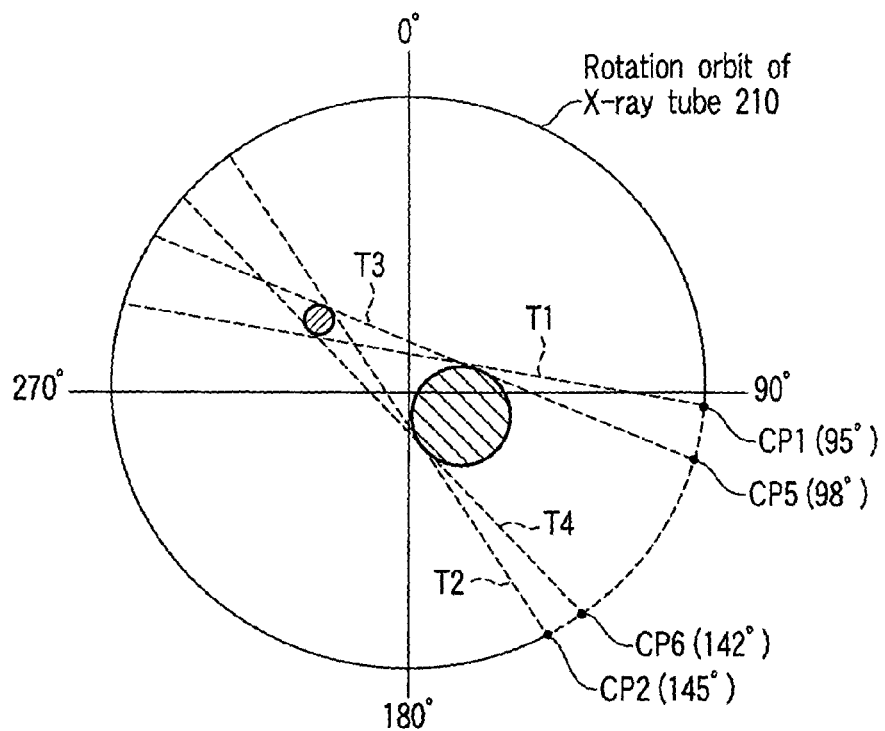
FIG. 23 is a supplementary diagram concerning another operation of S228 of FIG. 18.

FIG. 23 shows the micro sections. First, the micro section (initial irradiation limit period) from when the region to be treated starts entering the X-ray shade of the important region until the region to be treated completely enters the X-ray shade of the important region can be set as a section from the intersection CP1 of the boundary line T1 and rotation orbit to the intersection CP5 of the tangent T2 and rotation orbit. Similarly, the micro section (end period of the irradiation limit period) from when the region to be treated starts leaving from the X-ray shade of the important region until the region to be treated completely leaves the X-ray shade of the important region can be set as a section from the intersection CP6 of the tangent T4 and rotation orbit to the intersection CP2 of the boundary line T2 and rotation orbit.

In the same manner as in CP1, CP2, for the intersection CP5, the treatment planning system 2113 obtains two intersections of the tangent T2 and rotation orbit, selects the point in the vicinity of the middle position of the important region, and calculates the angle of the selected intersection CP5, for example, as 98°. Similarly, for the intersection CP6, the treatment planning system 2113 obtains two intersections of the tangent T4 and rotation orbit, selects the point in the vicinity of the middle position of the important region, and calculates the angle of the selected intersection CP5, for example, as 142°.

Figure 24:
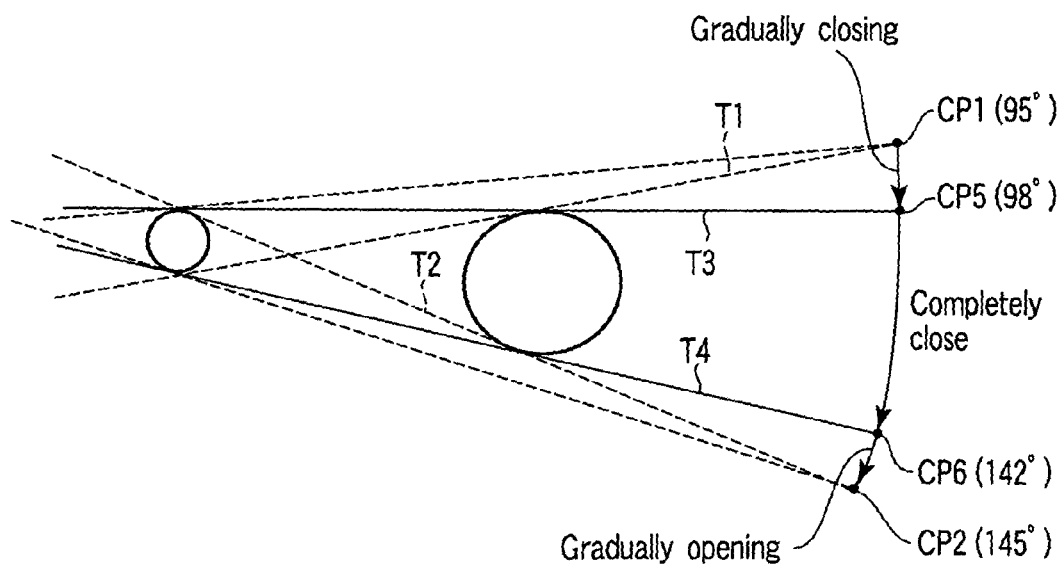
FIG. 24 is an explanatory view of another operation of S228 of FIG. 18.
Figure 25:
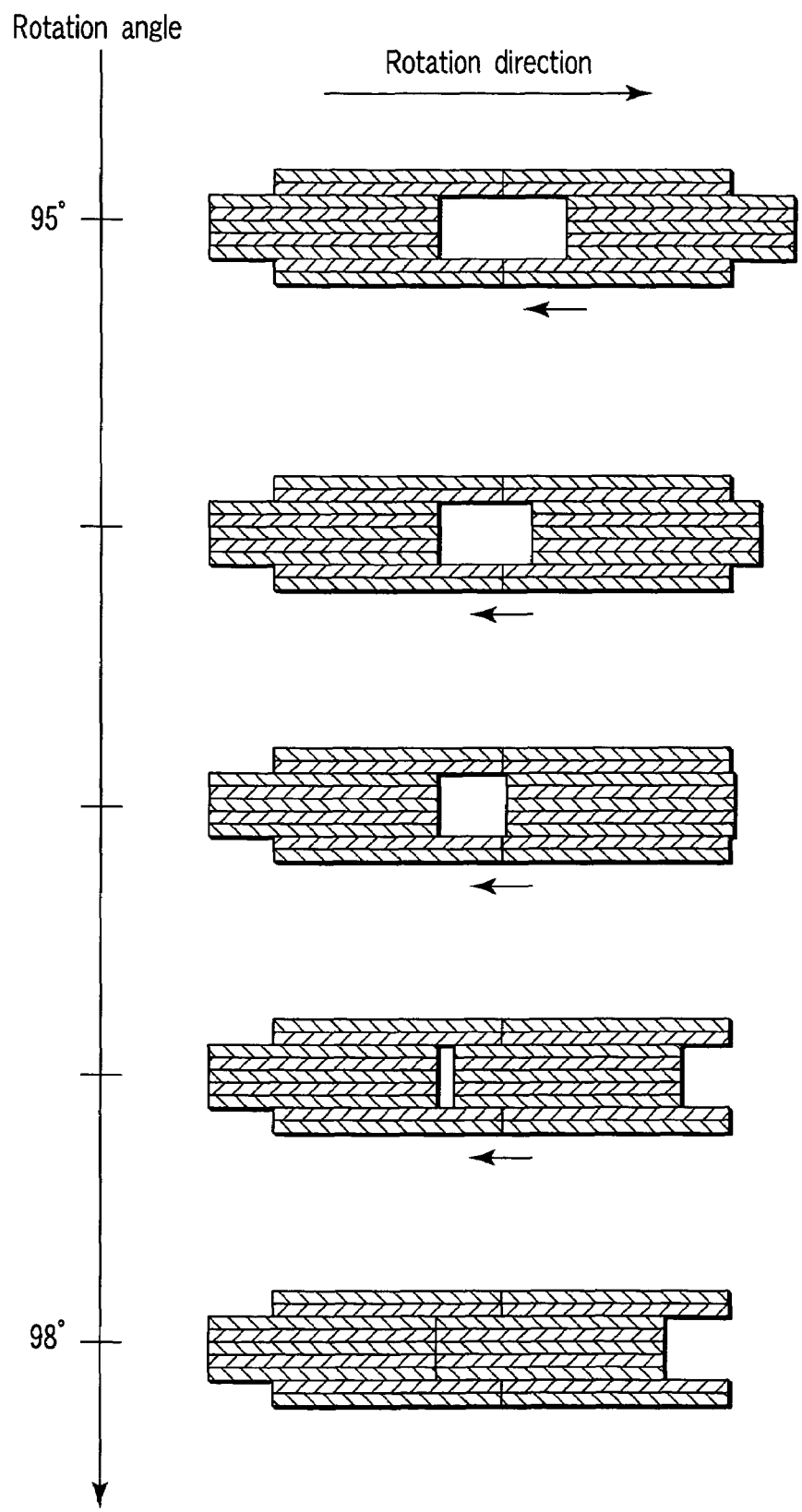
FIG. 25 is a diagram showing a closing operation of leaves between CP1 (95°) and CP5 (98°) of FIG. 24.

The treatment planning system 2113 dynamically controls the multi-leaf collimator driving unit 2107 in accordance with the rotation of the X-ray tube 2101. When the X-ray tube 2101 reaches the start point (95°) of the initial section shown in FIG. 24, the leaves of the multi-leaf collimator 2108 start closing. The aperture of the leaf is gradually closed with the rotation of the X-ray tube 2101. When the X-ray tube 2101 reaches the end point (98°) of the section, the respective leaves of the collimator 2108 are completely closed.

It is to be noted that as described above the leaves disposed opposite to each other form the pair, only one of the leaves of the pair is closed, and this leaf is disposed on a front side with respect to a rotation direction. The backward leaf with respect to the rotation direction is maintained at the aperture at the start point (95°) of the initial section.

The treatment planning system 2113 maintains the completely closed state of each leaf of the multi-leaf collimator 2108 in the section from the end point (98°) of the initial section to the start point (142°) of the latter section.

Figure 26:
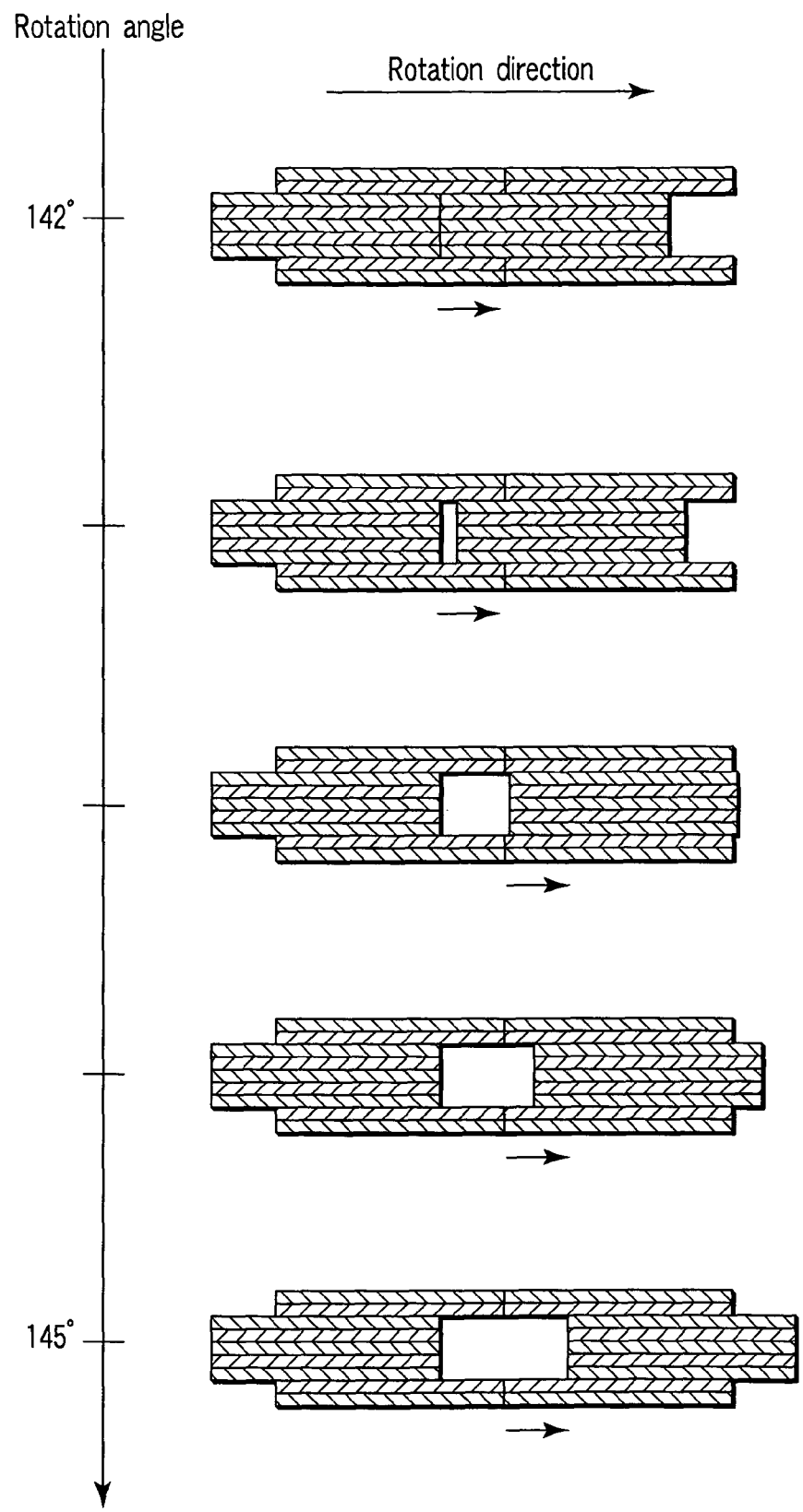
FIG. 26 is a diagram showing the closing operation of the leaves between CP2 (142°) and CP6 (145°) of FIG. 24.

Moreover, when the X-ray tube 2101 reaches the end point (142°) of the latter section, as shown in FIG. 26, the treatment planning system 2113 controls the multi-leaf collimator driving unit 2107 so as to slightly open the aperture of each leaf of the multi-leaf collimator 2108, gradually open the leaf together with the progress of the rotation of the leaves 2201, and open each leaf of the multi-leaf collimator 2108 in accordance with the end point (145°) of the latter section, when the tube reaches the end point (145°) of the latter section. The leaf to be opened is the closed leaf, that is, the leaf on the front side with respect to the rotation direction.

In this manner, when the fan angle of the X-ray is gradually closed in the initial section, and gradually opened in the latter section, the exposure reduction of the important region is maintained, and the treatment efficiency onto the region to be treated can further be enhanced.

Figure 17:
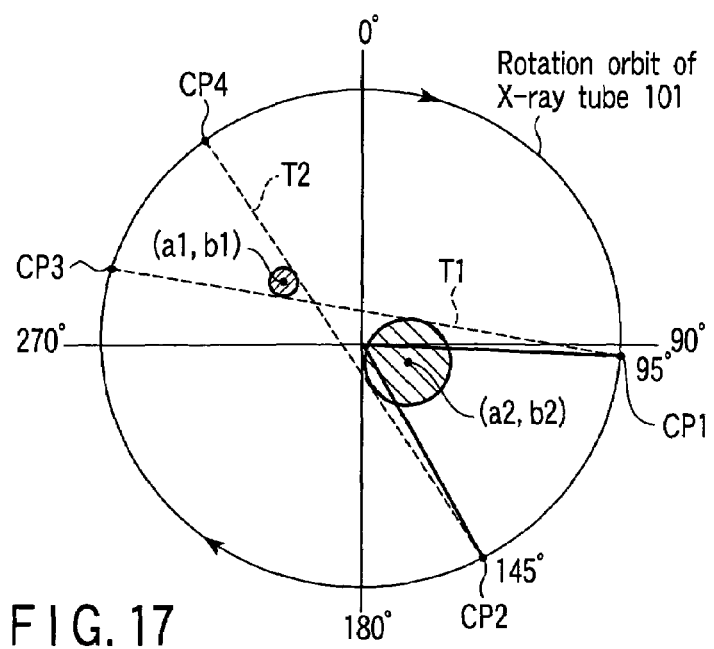
FIG. 17 is a supplementary diagram of S208 to S210 of FIG. 14.

In the example of FIG. 17, in the section including CP1 and CP2, the leaves of the multi-leaf collimator 2108 are closed in the state in which the generation of the X-rays is continued, but in this section the X-ray generation may also be halted in the same manner as in the example of FIG. 22. In this case, the supply of the filament current is preferably continued, while the application of the tube voltage is halted.

EMBODIMENT 3-1

Figure 27:
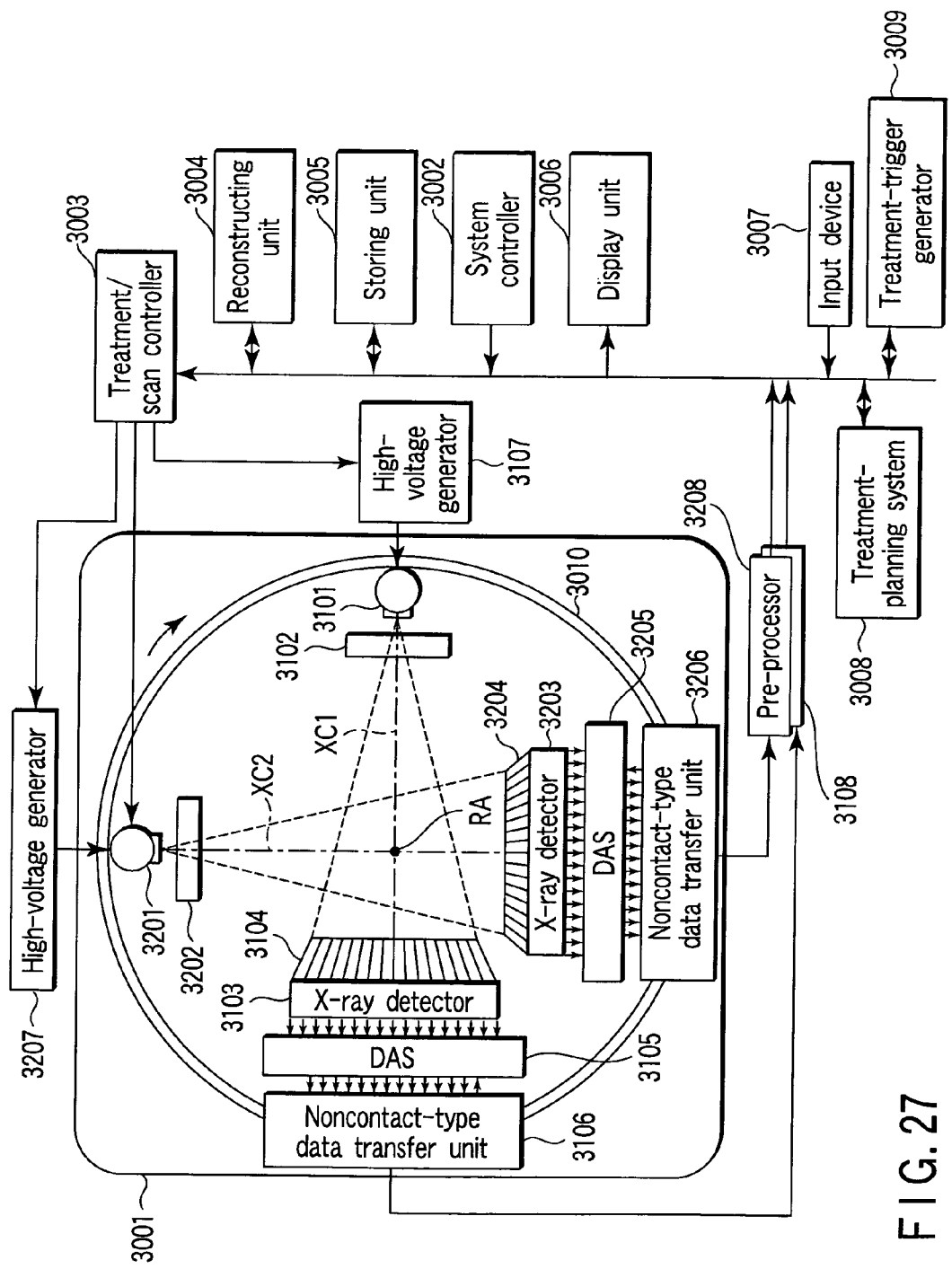
FIG. 27 is a diagram showing the constitution of the concentrated irradiation type radiotherapy apparatus according to Embodiment 3-1 of the present invention.

FIG. 27 is a diagram showing the constitution of the concentrated irradiation type radiotherapy apparatus according to Embodiment 3-1 of the present invention. The concentrated irradiation type radiotherapy apparatus according to Embodiment 3-1 includes a basic structure common to that of a two-tubes spherical X-ray computer tomography apparatus. The concentrated irradiation type radiotherapy apparatus includes a gantry 3001. The gantry 3001 includes a rotary ring 3010 held so as to be rotatable centering on the rotation center axis RA. The rotary ring 3010 includes first and second scanner systems. The first scanner system is for imaging, and the second scanner system is used for both the imaging and treatment. The first scanner system includes a first X-ray tube 3101 and a multi-channeled X-ray detector 3103 mounted on the rotary ring 3010. The first X-ray tube 3101 is attached in a direction opposite to the rotation center axis RA, that is, to a position where a center axis (X-ray center axis) XC1 of the X-ray flux from the X-ray tube 3101 crosses at right angles to the rotation center axis RA. The first X-ray tube 3101 receives the application of the tube voltage in accordance with the generation of a relatively low dose of X-rays for imaging and the supply of the filament current from a first high voltage generator 3107 to generate the relatively low dose of X-rays for imaging.

The multi-channeled X-ray detector 3103 is attached to the position on the rotary ring 3010 disposed opposite to the X-ray tube 3101 via the rotation center axis RA. The X-ray detector 3103 includes a plurality of X-ray detection devices arrayed in a direction substantially crossing at right angles to the rotation center axis RA and X-ray center axis XC1, in actual, along the circular arc centering on the X-ray focal point. The X-ray detector 3103 includes the single X-ray detection device array or the plurality of X-ray detection device arrays. The former is referred to as the X-ray detector for the single slice, and the latter is referred to as the X-ray detector for multi-slices or of the two-dimensional array type.

It is to be noted that the rotation center axis RA is assumed as the Z-axis, and the rotation coordinate system centering on the Z-axis is defined by an XYZ coordinate system. The XYZ coordinate systems are individually defined in the first and second scanner systems. In the first scanner system, the X-ray center axis XC1 is defined as the Y-axis, and the axis crossing at right angles to the ZY-axis is defined as the X-axis. In the second scanner system, the X-ray center axis XC2 is defined as the Y-axis, and the axis crossing at right angles to the ZY-axis is defined as the X-axis. The Z-axis is common to both coordinate systems.

A slit 3102 is disposed between the X-ray tube 3101 and the rotation center axis RA. In actual, the slit 3102 is attached to the X-ray radiation window of the X-ray tube 3101. Onto an X-ray incident surface of the X-ray detector 3103, a converging collimator 3104 is attached including a plurality of collimator plates whose angles are individually adjusted so as to converge the light on one point. The converging collimator 3104 is used having an optimal converging point depth such that a geometric converging point of the converging collimator 3104 agrees with the X-ray focal point of the X-ray tube 3101. The converging collimator 3104 includes a scattered ray removing function higher than that of a collimator 3204 of the second scanner system.

The first X-ray detector 3103 is generally connected to a data collection circuit 3105 generally called the data acquisition system (DAS). The data collection circuit 3105 includes a function of converting the output (current signal) of each channel of the X-ray detector 3103 to the voltage signal, amplifying the signal, and converting the signal to the digital signal. The DAS 3105 is connected to a pre-processor 3108 for correcting the non-uniformity between the channels of DAS outputs via a noncontact type data transfer unit 3106 in which the light and magnetism are mediums. The pre-processed data (projection data) is stored in an auxiliary storing unit 3005.

The second scanner system for use in both the imaging and treatment includes a second X-ray tube 3201 and a multi-channeled X-ray detector 3203 mounted on a position on the rotary ring 3010 where an X-ray center axis XC2 crosses at right angles to the X-ray center axis XC1 of the first scanner system on the rotation center axis RA.

A second high voltage generator 3207 selectively generates relatively low tube voltage and filament current, and relatively high tube voltage and filament current. The relatively low tube voltage and filament current generate the relatively low dose of X-rays for the imaging. The relatively high tube voltage and filament current generate a relatively high dose of X-rays for the treatment.

The second X-ray tube 3201 receives the application of the relatively low tube voltage and the supply of the filament current from the second high voltage generator 3207 to generate the relatively low dose of X-rays for the imaging. The second X-ray tube 3201 receives the application of the relatively high tube voltage and the supply of the filament current from the second high voltage generator 3207 to generate the relatively high dose of X-rays for the treatment.

The second X-ray detector 3203 includes a plurality of X-ray detection devices arrayed in a direction substantially crossing at right angles to the rotation center axis RA and X-ray center axis XC2, in actual, along the circular arc centering on the X-ray focal point. The X-ray detector 3203 includes the single X-ray detection device array or the plurality of X-ray detection device arrays. The former is referred to as the X-ray detector for the single slice, and the latter is referred to as the X-ray detector for the multi-slices or of the two-dimensional array type.

Figure 28:
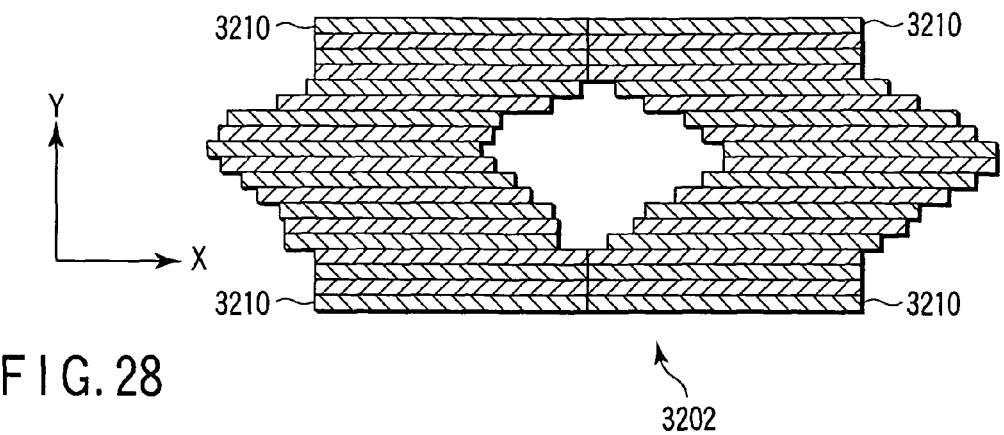
FIG. 28 is a plan view showing the structure of the multi-leaf collimator of FIG. 27.

A multi-leaf collimator 3202 is disposed between the second X-ray tube 3201 and the rotation center axis RA. In actual, the multi-leaf collimator 3202 is attached to the X-ray radiation window of the second X-ray tube 3201. As shown in FIG. 28, the multi-leaf collimator 3202 includes a plurality of leaves 3210 each of which is disposed to be movable forwards/backwards along the X-axis and each of which has the strip shape having a width of 1 mm in the converted value on the rotation center axis RA. In actual, assuming that the X-ray center axis XC2 is the center line, two leaves 3210 constitute the pair so as to open on either side via the center line. A plurality of leaf pairs, nine pairs here are juxtaposed in an Z-axis direction.

Onto the X-ray incident surface of the second X-ray detector 3203, a converging collimator 3204 is attached including a plurality of collimator plates whose angles are individually adjusted so as to converge the light on one point. The converging collimator 3204 is used having an optimal converging point depth such that the geometric converging point of the converging collimator 3204 agrees with the X-ray focal point of the second X-ray tube 3201. The converging collimator 3204 has a general height of 30 mm.

The second X-ray detector 3203 is generally connected to a data collection circuit 3205. The data collection circuit 3205 includes a function of converting the output (current signal) of each channel of the X-ray detector 3203 to the voltage signal, amplifying the signal, and converting the signal to the digital signal. The DAS 3205 is connected to a pre-processor 3208 for correcting the non-uniformity between the channels of DAS outputs via a noncontact type data transfer unit 3206 in which the light and magnetism are mediums. The pre-processed data (projection data) is stored in the auxiliary storing unit 3005.

The auxiliary storing unit 3005 is connected to an image reconstructing unit 3004 for reconstructing the image data from the projection data, a display unit 3006, an input device 3007 including the pointing devices such as the mouse and the keyboard, a treatment planning system 3008, a treatment trigger generator 3009, a treatment/scan controller 3003 for controlling the gantry 3001 and high voltage generators 3107, 3207 to execute the treatment in accordance with the treatment plan, and a system controller 3002 via the data/control bus.

The treatment planning system 3008 calculates the internal dose distribution of radioactive rays based on the X-ray output dose characteristic data and tomographic image data. The treatment planning system 3008 calculates the relation between the aperture of the multi-leaf collimator 3202 and the X-ray tube rotation angle with respect to the region to be treated set via the input device 3007.

During pre-scanning before the treatment, the image reconstructing unit 3004 immediately reconstructs the image data based on the projection data collected via the first scanner system. The image data is immediately supplied to the treatment trigger generator 3009.

The treatment trigger generator 3009 extracts pixel values (CT values) of a plurality of pixels in a region of interest including the region to be treated from the image data. The treatment trigger generator 3009 compares the extracted pixel values, average value, or maximum value with a predetermined threshold value (first threshold value). Here, the average value is assumed. The treatment trigger generator 3009 generates a treatment trigger signal, when the average value reaches or exceeds the threshold value.

Moreover, the treatment trigger generator 3009 extracts the pixel values (CT values) of a plurality of pixels in the region of interest including the region to be treated from the image data generated in the treatment period. The treatment trigger generator 3009 compares the extracted pixel values, average value, or maximum value with the predetermined threshold value. Here, the average value is assumed. The treatment trigger generator 3009 generates a treatment finish signal, when the average value reaches or exceeds the threshold value (second threshold value). The second threshold value is higher than the first threshold value.

It is to be noted that in the treatment period, the relatively high dose of X-rays for the treatment are generated from the second X-ray tube 3201 of the second scanner system, and some of scattered rays reach the first X-ray detector 3103 of the first scanner system. As described above, the 60 mm or higher converging collimator 3104 is attached to the first X-ray detector 3103 of the first scanner system to enhance the scattered ray removing function, but it is actually impossible to zero scattered ray incidence. Therefore, in the treatment period, some of the scattered rays of the X-rays for the treatment generated from the second X-ray tube 3201 of the second scanner system reach the first X-ray detector 3103 of the first scanner system, and the CT value is raised to a value higher than that before the treatment. Therefore, typically the threshold value for the treatment end (second threshold value) is set to be higher than that for the treatment start (first threshold value).

Moreover, a timing for starting the treatment is obtained in comparison with the threshold value for the treatment start. On the other hand, the treatment end may be managed by a time elapsed from the treatment start, not by the comparison with the threshold value for the treatment end. That is, the treatment may be ended, when the time elapsed from the treatment start reaches the initially set treatment time.

Figure 30A:
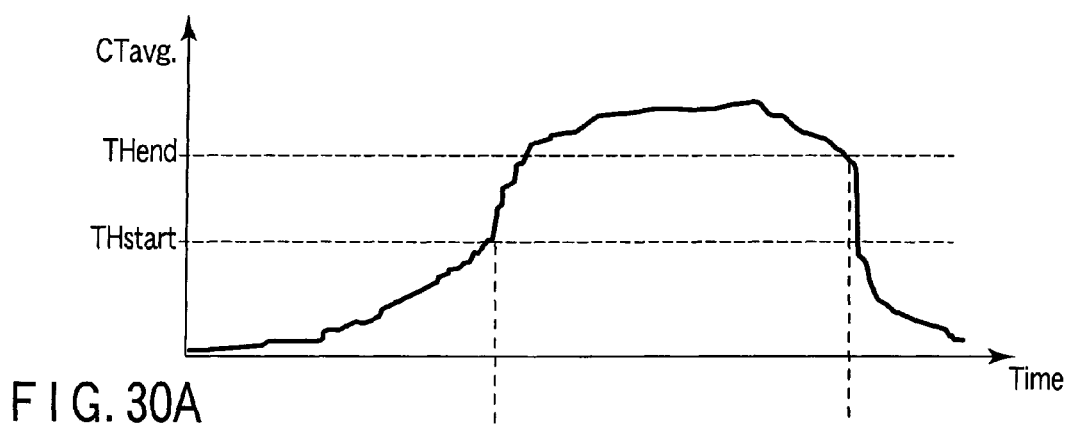
FIG. 30A is a time chart showing changes of a CT value average with an elapse of time in and after pre-scan start in Embodiment 3-1.
Figure 30B:
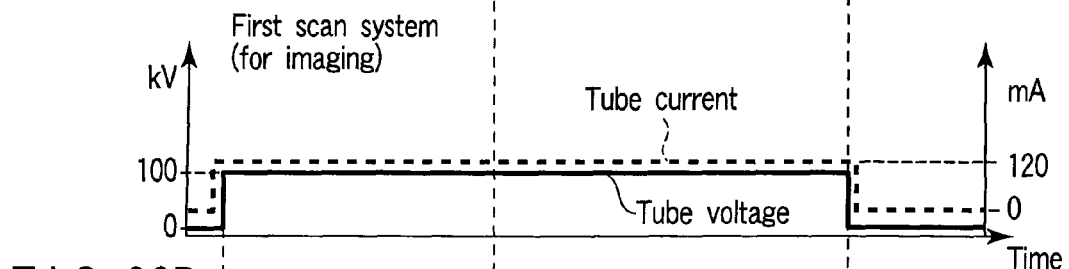
FIG. 30B is a time chart showing changes of a tube voltage and current of the X-ray tube of a first scanner system for imaging with the elapse of time in Embodiment 3-1.
Figure 30C:
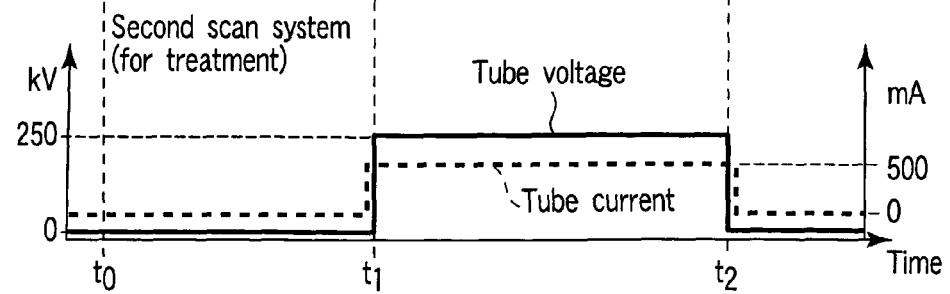
FIG. 30C is a time chart showing changes of the tube voltage and current of the X-ray tube of a second scanner system for treatment with the elapse of time in Embodiment 3-1.
Figure 29:
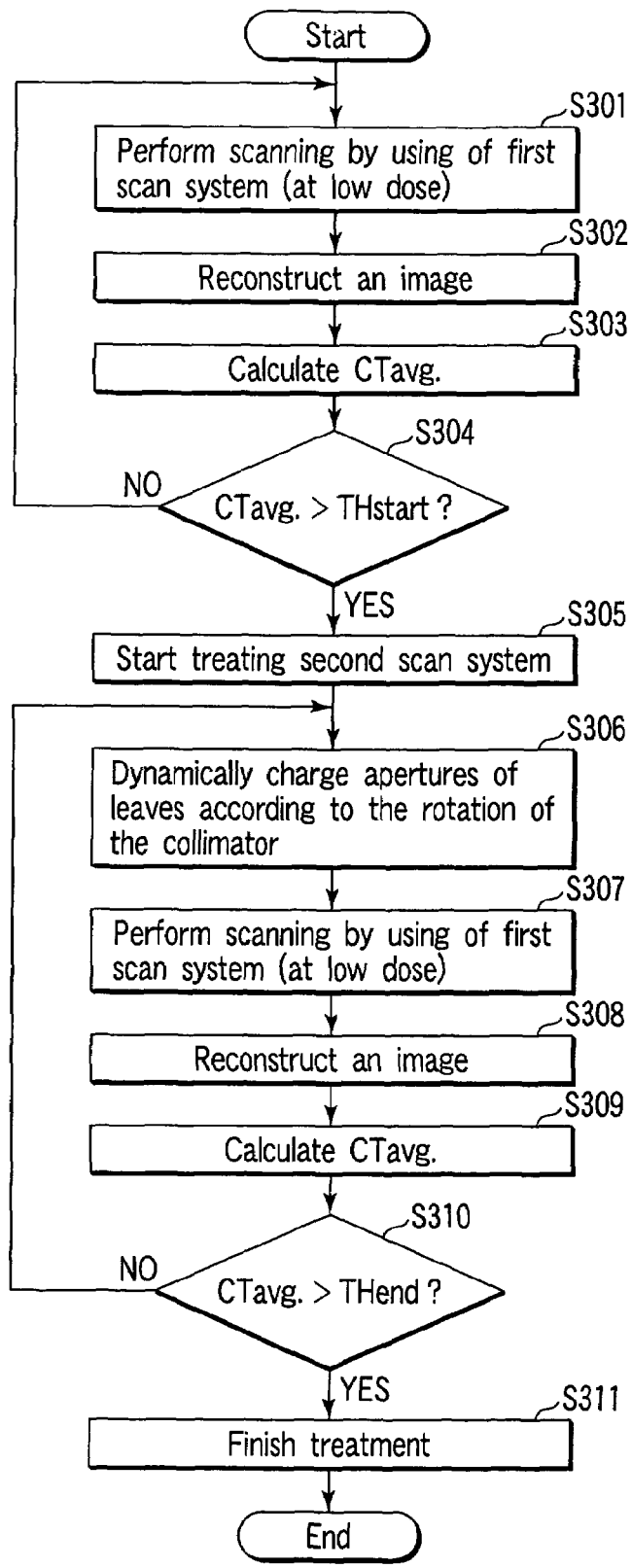
FIG. 29 is a flowchart showing a series of flows from pre-scan till treatment finish in Embodiment 3-1.

FIG. 29 shows the flow of a series of operations required for the treatment finish in Embodiment 3-1. FIG. 30 shows changes of a CT value average with an elapse of time in and after pre-scan start, changes of the tube voltage and current of the X-ray tube of the first scanner system for the imaging with the elapse of time, and changes of the tube voltage and current of the X-ray tube of the second scanner system for the treatment with the elapse of time. FIG. 32 shows X-ray irradiation states of the first and second scanner systems in a period between a pre-scan start time t0 and treatment start time t1.

Before the treatment, contrast media is injected into the subject. As described above, while injecting the contrast media, the irradiation of X-rays for the treatment is carried out. It is known that, in this case, the treatment effect is enhanced by secondary electrons discharged from the contrast media by a photoelectric effect. To enhance the treatment efficiency, it is effective to radiate the X-rays for the treatment in a period when the contrast media exists in a certain degree of concentration in the region to be treated. For this, the contrast media concentration of the region to be treated is immediately monitored in the first scanner system before the treatment start, and the treatment starts, when the concentration rises to a certain degree.

First at time t0, the pre-scan is started. In the pre-scan, the high voltage is not applied to the second X-ray tube 3201 of the second scanner system, and the relatively high dose of X-rays for the treatment are not generated. On the other hand, the scanning is performed with the low dose in the first scanner system. That is, a relatively low high-voltage, for example, of 100 kV is applied to the first X-ray tube 3101 from the first high voltage generator 3107, and a relatively low tube current, for example, of 120 mA is passed by the supply control of the filament current. Accordingly, the relatively low dose of X-rays for the imaging are generated from the first X-ray tube 3101 of the first scanner system. The X-rays transmitted through the subject are detected by the first X-ray detector 3103. This detection is repeated at a constant frequency together with the rotation of the rotary ring 3010. Every rotation by a given angle, the projection data for the angle required for reconstructing the image data is obtained (S301). The image reconstructing unit 3004 immediately reconstructs the image data based on the collected projection data (S302). The image data is displayed in the display unit 3006 and sent to the treatment trigger generator 3009.

Figure 31:
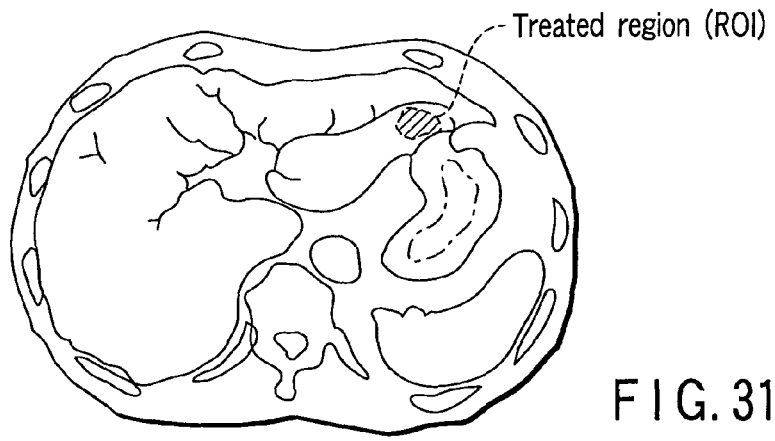
FIG. 31 is a diagram showing an example of a region of interest (ROI) of S303 of FIG. 29.
Figure 32A:
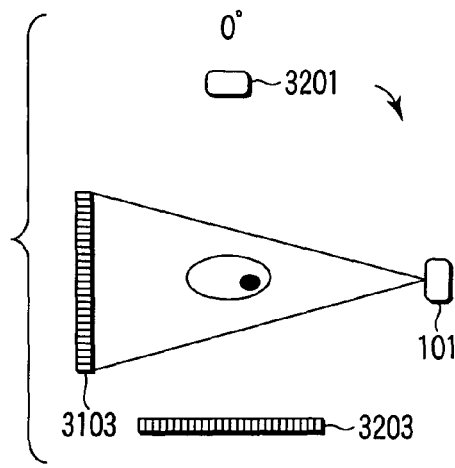
FIGS. 32A to 32D are diagrams showing X-ray irradiation states of the first and second scanner systems in a period between a pre-scan start time t0 and treatment start time t1 of FIG. 30.
Figure 32B:
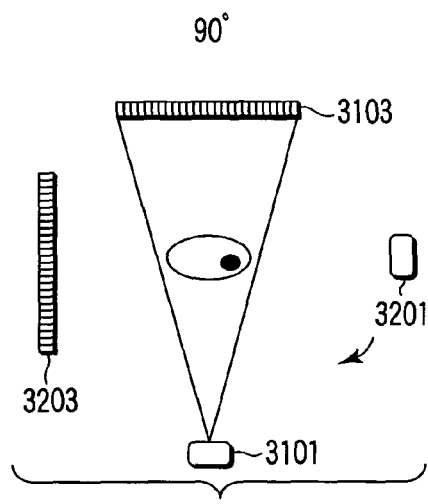
Figure 32C:
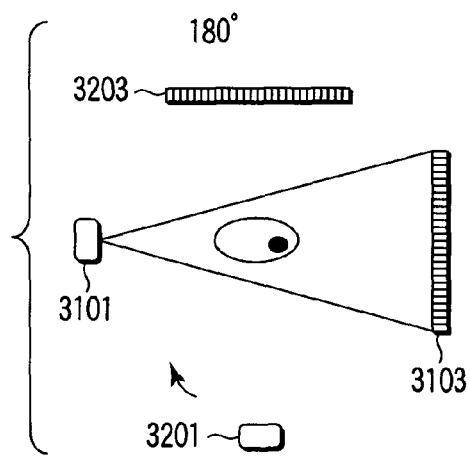
Figure 32D:
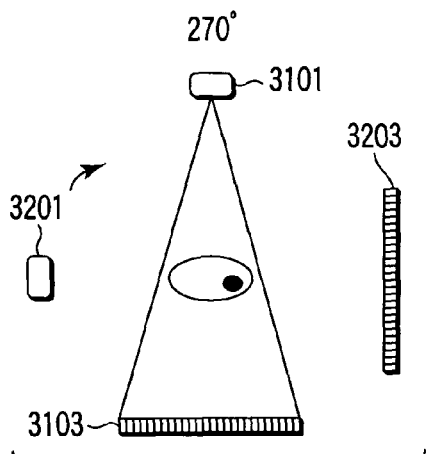
Figure 33A:
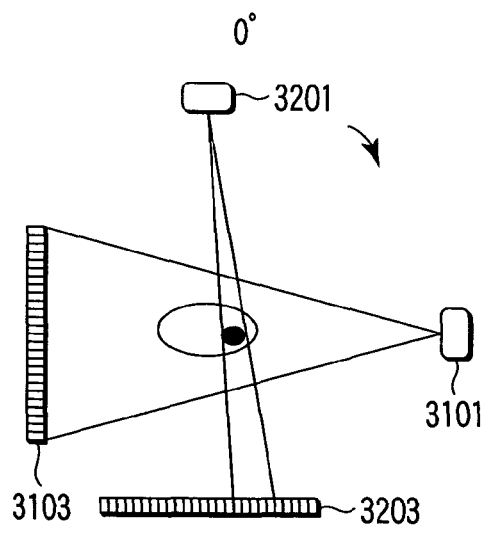
FIGS. 33A to 33D are diagrams showing the X-ray irradiation states of the first and second scanner systems in the period between the treatment start time t1 and a treatment finish time t2 of FIG. 30.
Figure 33B:
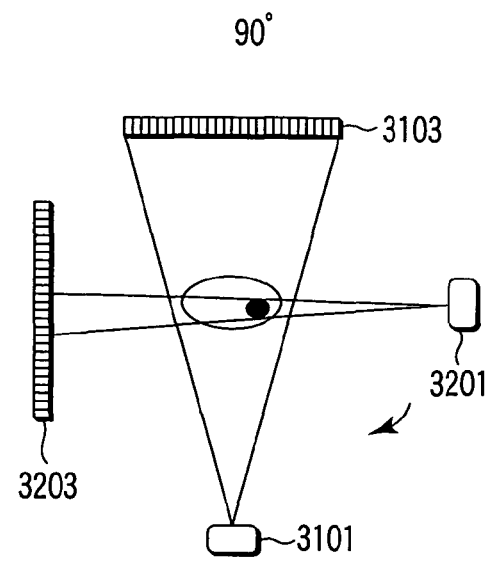
Figure 33C:
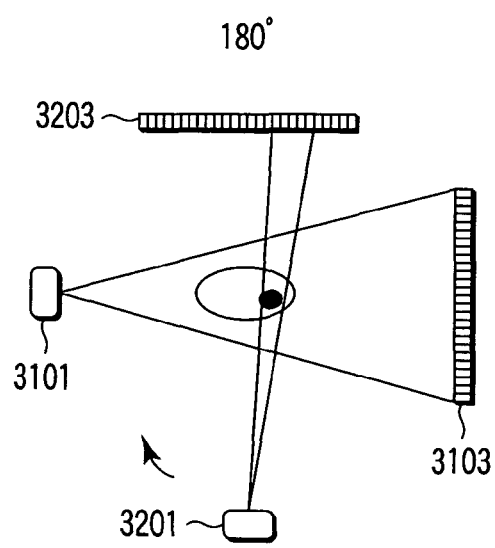
Figure 33D:
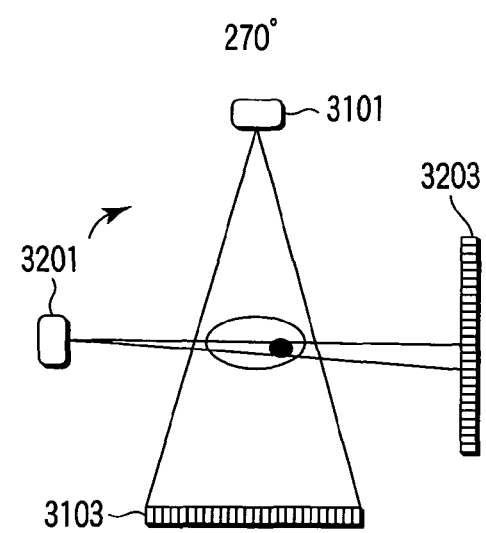

In the treatment trigger generator 3009, the pixel values (CT values) of the plurality of pixels in the region of interest including the region to be treated shown in FIG. 31, which is set beforehand via the input device 3007, are extracted from the image data. For example, an average value CTavg. is calculated (S303). Moreover, in the treatment trigger generator 3009, the calculated average value CTavg. is compared with the predetermined threshold value for starting the treatment (S304). When the average value CTavg. is lower than the threshold value for starting the treatment, it is meant that the contrast media does not sufficiently flow in the region of interest. The reaching of exceeding of the average value CTavg. with respect to the threshold value for starting the treatment means that the contrast media sufficiently flow in the region of interest.

When the average value CTavg. is lower than the threshold value for starting the treatment, the process of S301 to S304 is repeated. With the elapse of time, an inflow amount of the contrast media into the region of interest increases. When the average value CTavg. reaches or exceeds the threshold value for starting the treatment, the treatment trigger signal is generated from the treatment trigger generator 3009. The treatment is started under the control of the treatment/scan controller 3003 in accordance with the treatment trigger signal. That is, a relatively high voltage, for example, of 250 kV is applied to the second X-ray tube 3201 from the second high voltage generator 3207, and a relatively high tube current, for example, of 500 mA is passed by the supply control of the filament current. Accordingly, the relatively high dose of X-rays for the imaging are generated from the second X-ray tube 3201 of the second scanner system, and the region to be treated of the subject is irradiated with the relatively high dose of X-rays for the treatment finely shaped by the aperture of the multi-leaf collimator 3202 in accordance with the region to be treated. As shown in FIG. 33, the aperture of each leaf of the multi-leaf collimator 3202 is dynamically changed in accordance with the rotation angle of the second X-ray tube 3201 (S306). Accordingly, the rotation is involved to selectively irradiate the region to be treated with the X-rays for the treatment.

Even in and after the treatment start, the scanning in the first scanner system, that is, the collection of the projection data (S307), the immediate reconstructing of the image data (S308), the immediate display of the image data, and the calculation of the CT average value CTavg. of the region of interest (S309) are continued. In the treatment period, in the treatment trigger generator 3009, the calculated average value CTavg. is compared with a threshold value THend for finishing the treatment, which is set to be higher than the predetermined threshold value for starting the treatment (S310).

The average value CTavg. higher than the threshold value for finishing the treatment means that the contrast media exists in the concentration sufficiently for fulfilling a given treatment effect in the region of interest. When the average value CTavg. reaches or becomes lower than the threshold value for finishing the treatment, it is meant that the contrast media flows out of the region of interest, the concentration drops, and the given treatment effect cannot be fulfilled.

When the average value CTavg. is higher than the threshold value for finishing the treatment, the irradiation of the X-rays for the treatment is continued, and the process of S306 to S310 is repeated. When the average value CTavg. reaches or goes below the threshold value for finishing the treatment, the treatment finish signal is generated from the treatment trigger generator 3009.

In response to this treatment finish signal, the application of the high voltage and the supply of the filament current to the second X-ray tube 3201 from the second high voltage generator 3207 are stopped. In response to the treatment finish signal, the application of the high voltage and the supply of the filament current to the first X-ray tube 3101 from the first high voltage generator 3107 are stopped. Accordingly, the treatment is finished (S311).

It is to be noted that the timing for starting the treatment is obtained in comparison with the threshold value for starting the treatment. On the other hand, the treatment may be ended, when the time elapsed from the treatment start reaches the initially set treatment time.

Moreover, in the treatment/scan controller 3003, a signal indicating the injection state of the contrast media is inputted from an injector (not shown), and the treatment and irradiation may be stopped in accordance with the injection state. For example, when the injection of a predetermined amount of contrast media from the injector is completed, the treatment/scan controller 3003 finishes the treatment at this time or after the elapse of a predetermined time. When the injection of the contrast media is stopped by trouble of the injector, the treatment/scan controller 3003 stops the application of the high voltage and the supply of the filament current to the second X-ray tube 3201 from the second high voltage generator 3207 in emergency, and stops the irradiation of the subject with the X-rays for the treatment in emergency. For the emergency stop, together with the stopping of the application of the high voltage and the supply of the filament current to the second X-ray tube 3201 from the second high voltage generator 3207, the irradiation may also be stopped by an X-ray shutter mechanism.

In this manner, according to Embodiment 3-1, the contrast media concentration of the region of interest is monitored, and the treatment is started when the concentration rises. When the contrast media concentration drops, the treatment is finished. Accordingly, the time deviation in the treatment start is reduced, and a high treatment efficiency can be realized. Since a section including the region to be treated can visually be confirmed with the image over the treatment period from the pre-scan, the operator can actually visually confirm the progress situation of the treatment.

It is to be noted that in the above description the treatment is finished, when the average value CTavg. reaches or goes below the threshold value for finishing the treatment. However, a treatment finish time may also be determined by the time elapsed from the treatment start.

Moreover, the treatment finish time is managed by an accumulated time of the X-ray irradiation for the treatment from the treatment start, and further the concentration of the contrast media is monitored. Only in a period when the average value CTavg. is higher than the threshold value for finishing the treatment (threshold value for halting the treatment in this case), the X-rays for the treatment are radiated. On the other hand, in a period when the average value CTavg. reaches or goes below the threshold value for halting the treatment, the irradiation with the X-rays for the treatment is halted. That is, only in a period when a high treatment effect can be fulfilled, the X-rays for the treatment are generated, and accordingly the high treatment efficiency can be maintained.

EMBODIMENT 3-2

The concentrated irradiation type radiotherapy apparatus according to Embodiment 3-1 includes the basic structure common to that of the two-tubes spherical X-ray computer tomography apparatus, but the concentrated irradiation type radiotherapy apparatus according to Embodiment 3-2 includes a basic structure common to that of a one-tube spherical X-ray computer tomography apparatus. The concentrated irradiation type radiotherapy apparatus of Embodiment 3-2 realizes the function of monitoring the concentration of the contrast media in the same manner as in Embodiment 3-1.

Figure 34:
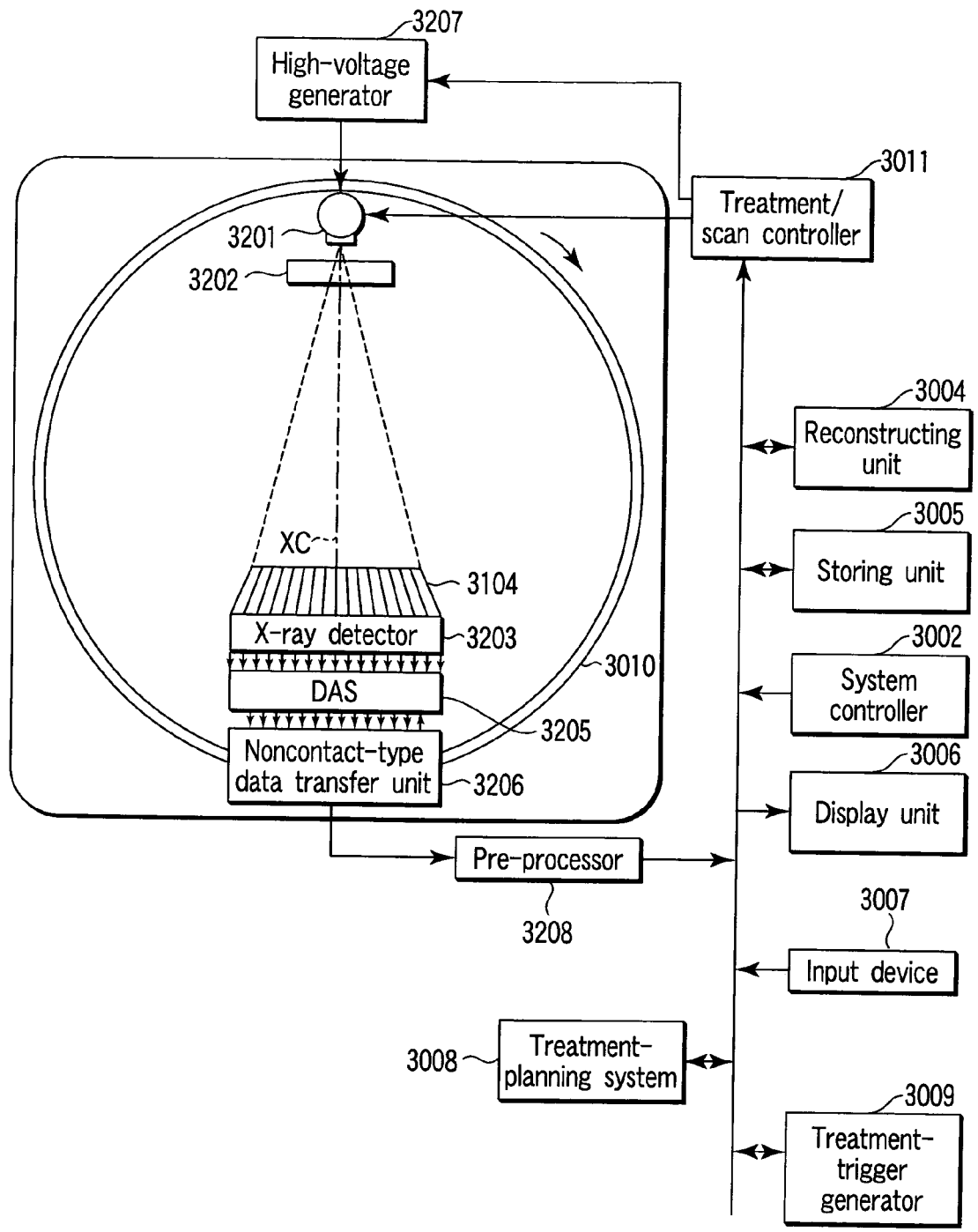
FIG. 34 is a diagram showing the constitution of the concentrated irradiation type radiotherapy apparatus according to Embodiment 3-2 of the present invention.
Figure 38A:
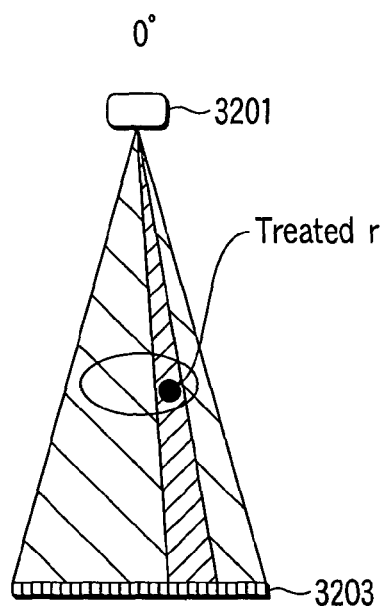
FIGS. 38A to 38D are diagrams showing the X-ray irradiation state in the period between the treatment start time and treatment finish time in Embodiment 3-2.
Figure 38B:
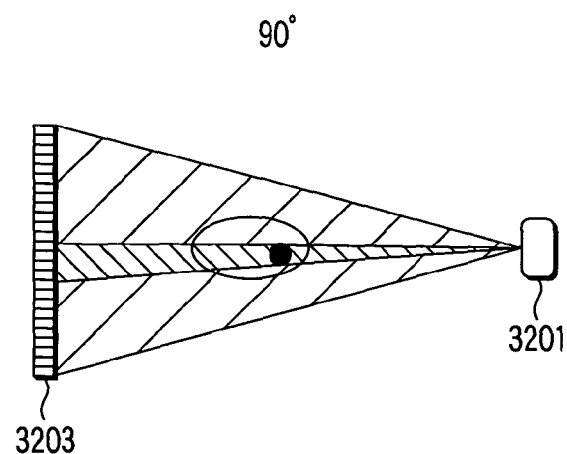
Figure 38C:
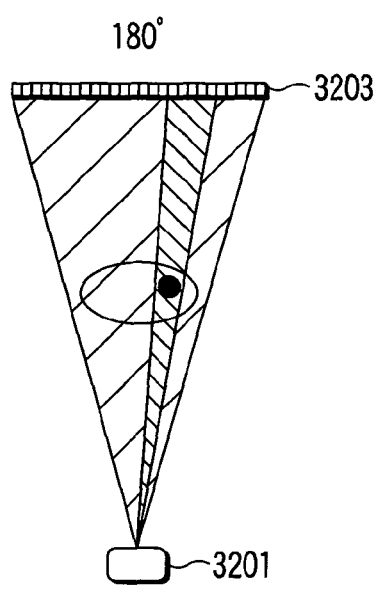
Figure 38D:
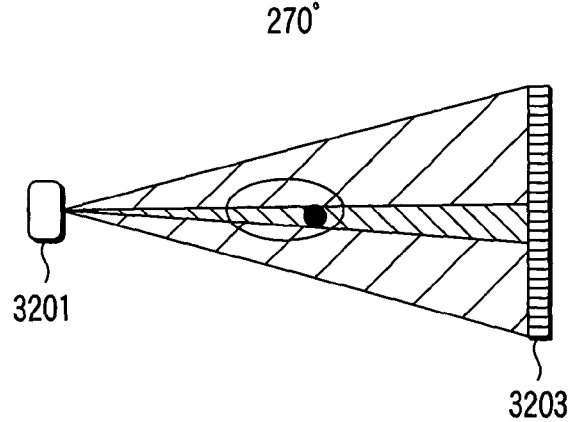

FIG. 34 shows the constitution of the concentrated irradiation type radiotherapy apparatus of Embodiment 3-2. In FIG. 34, the same constituting elements as those of FIG. 27 are denoted with the same reference numerals. The concentrated irradiation type radiotherapy apparatus of Embodiment 3-2 singly includes the second scanner system for use in both the imaging and the treatment according to Embodiment 3-1. That is, the X-ray tube 3201 and the multi-channeled X-ray detector 3203 are mounted on the rotary ring 3010. The relatively low tube voltage and filament current corresponding to the generation of the relatively low dose of the X-rays for the imaging, and the relatively high tube voltage and filament current corresponding to the generation of the relatively high dose of the X-rays for the treatment are selectively supplied to the X-ray tube 3201 from the high voltage generator 3207. The X-ray tube 3201 receives the application of the tube voltage and the supply of the filament current corresponding to the generation of the relatively low tube dose of the X-rays for the imaging from the high voltage generator 3207 to generate the relatively low dose of the X-rays for the imaging. The X-ray tube 3201 receives the application of the tube voltage and the supply of the filament current corresponding to the generation of the relatively high dose of the X-rays for the treatment from the high voltage generator 3207 to generate the relatively high dose of the X-rays for the treatment. Onto the X-ray incident surface of the X-ray detector 3203, the converging collimator 3104 having a height, for example, of 60 mm is attached including a high scattered ray removing current.

A treatment/scan controller 3011 controls the high voltage generator 3207 in the pre-scan period to supply the relatively low tube voltage and filament current to the X-ray tube 3201 in accordance with the generation of the relatively low dose of X-rays for the imaging. At the treatment start time, the treatment/scan controller 3011 controls the high voltage generator 3207 to switch the supply of the relatively low tube voltage and filament current in accordance with the generation of the relatively low dose of X-rays for the imaging to the supply of the relatively high tube voltage and filament current in accordance with the generation of the relatively high dose of X-rays for the treatment. The treatment/scan controller 3011 fully opens several leaves in the middle of the multi-leaf collimator 3202, and completely closes the other leaves. Moreover, at the treatment start time, the treatment/scan controller 3011 maintains the full opening of only one leaf in the middle of the multi-leaf collimator 3202, and further adjusts the apertures of the other leaves in accordance with the shape or position of the region to be treated.

FIG. 35 shows the flow of a series of operations required for the treatment in Embodiment 3-2. FIG. 37 shows changes of the CT value average in and after the pre-scan start and those of the tube voltage and current of the X-ray tube 3201 with the elapse of time. Before the treatment, the contrast media is injected into the subject, and the pre-scan is started at the time t0. At this time, as shown in FIG. 36A. some leaves, three leaves in the middle of the multi-leaf collimator 3202 are fully opened, and the other leaves are completely closed (S321).

In the pre-scan, the relatively low high-voltage, for example, of 100 kV is applied to the X-ray tube 3201 from the high voltage generator 3207, and a relatively low tube current, for example, of 120 mA is passed by the supply control of the filament current. Accordingly, the relatively low dose of X-rays for the imaging are generated from the X-ray tube 3201. The X-rays are shaped to be thin by a fine slit formed by the fully opened three leaves. The subject is irradiated with the fan-shaped X-rays. The X-rays transmitted through the subject are detected by the X-ray detector 3203. This detection is repeated at the constant frequency together with the rotation of the rotary ring 3010. Every rotation by a given angle, the projection data for the angle required for reconstructing the image data is obtained (S322). The image reconstructing unit 3004 immediately reconstructs the image data based on the collected projection data (S323). The image data is displayed in the display unit 3006 and sent to the treatment trigger generator 3009.

In the treatment trigger generator 3009, the pixel values (CT values) of the plurality of pixels in the region of interest including the region to be treated are extracted from the image data and, for example, the average value CTavg. is calculated (S324). Moreover, in the treatment trigger generator 3009, the calculated average value CTavg. is compared with the predetermined threshold value for starting the treatment (S325).

When the average value CTavg. is lower than the threshold value for starting the treatment, the process of S322 to S325 is repeated. With the elapse of time, the inflow amount of the contrast media into the region of interest increases. When the average value CTavg. reaches or exceeds the threshold value for starting the treatment, the treatment trigger signal is generated from the treatment trigger generator 3009.

In response to the treatment trigger signal, the relatively high voltage, for example, of 250 kV is applied to the X-ray tube 3201 from the high voltage generator 3207, and the tube current is set to be relatively high, for example, 500 mA for the treatment. Accordingly, the treatment by the relatively high dose of X-rays is started (S326). With the switch of the tube voltage and current, under the control of the treatment/scan controller 3011, as shown in FIG. 36B, only one leaf in the middle of the multi-leaf collimator 3202 is maintained to be fully open, and the apertures of the other leaves are adjusted in accordance with the shape or position of the region to be treated (S327). By this aperture adjustment, as shown in FIG. 37, in a state in which the thin fan-shaped X-ray for the imaging is superposed upon the beamed X-ray for the treatment, the subject is irradiated with the X-rays.

Even in the treatment period, in the same manner as in the pre-scanning, the projection data is collected, and the image data is immediately reconstructed based on the collected projection data by the image reconstructing unit 3004 (S328).

In the treatment period, only one leaf in the middle, less than the number of leaves at the pre-scan time, is maintained to be fully open. The X-rays are thinly narrowed. The thin X-rays do not saturate the dynamic ranges of the detector 3203 and DAS 3205. A shaded image can be generated. Additionally, the X-rays radiated through the aperture formed by the other leaves whose apertures are adjusted in accordance with the shape or position of the region to be treated probably saturate the dynamic range of the corresponding channel. By the saturation of the dynamic range, blackout occurs in a region in which the thin X-rays for the treatment are concentrated. The region where the blackout occurs can be recognized as the region where the X-rays for the treatment are concentrated, and the positional deviation between the region and the region to be treated can be confirmed. On the other hand, an X-ray absorption factor distribution can be imaged in a region other than the region where the thin X-rays for the treatment are concentrated.

The reconstructed image data is displayed in the display unit 3006 and sent to the treatment trigger generator 3009. In the treatment trigger generator 3009, the pixel values (CT values) of the plurality of pixels in a peripheral region not causing the blackout, not in the region of interest including the region to be treated, are extracted from the image data, and the average value CTavg. is calculated (S329).

In the treatment trigger generator 3009, the calculated average value CTavg. is compared with the threshold value THend for finishing the treatment (S330). When the average value CTavg. is higher than the threshold value THend for finishing the treatment, the irradiation of the X-rays for the treatment is continued. That is, the process of S327 to S330 is repeated. When the average value CTavg. reaches or goes below the threshold value for finishing the treatment, the treatment finish signal is generated from the treatment trigger generator 3009. In response to this treatment finish signal, the application of the high voltage and the supply of the filament current to the X-ray tube 3201 from the high voltage generator 3207 are stopped. Accordingly, the treatment is finished (S331).

In this manner, according to Embodiment 3-2, the concentration of the contrast media in the region of interest is monitored. The treatment is started when the concentration rises. When the concentration of the contrast media drops, the treatment is finished. The time deviation at the treatment start is reduced. Accordingly, the high treatment efficiency can be realized. The section including the region to be treated is imaged over the treatment period from the pre-scan, and the operator can visually confirm the progress of the treatment. Since the region including the concentrated beamed thin X-rays for the treatment causes the blackout, the positional deviation of the region to be treated with respect to the concentration region can visually be confirmed.

It is to be noted that, in the same manner as in Embodiment 3-1, the treatment is finished as described above, when the average value CTavg. reaches or goes below the threshold value for finishing the treatment. However, the treatment finish time may also be determined by the time elapsed from the treatment start.

Moreover, in the same manner as in Embodiment 3-1, the treatment finish time is managed by the accumulated time of the X-ray irradiation for the treatment from the treatment start, and further the concentration of the contrast media is monitored. Only in the period when the average value CTavg. is higher than the threshold value for finishing the treatment (threshold value for halting the treatment in this case), the X-rays for the treatment are radiated. On the other hand, in the period when the average value CTavg. reaches or goes below the threshold value for halting the treatment, the irradiation with the X-rays for the treatment is halted. That is, only in the period when the high treatment effect can be fulfilled, the X-rays for the treatment are generated, and accordingly the high treatment efficiency can be maintained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A concentrated irradiation type radiotherapy apparatus, comprising:

a radiation source configured to generate radioactive rays in a beam direction for both treatment and imaging;

a radiation detector configured to detect radioactive rays transmitted through a subject;

a rotating mechanism configured to rotate the radiation source and the radiation detector about a rotating axis;

a reconstruction unit configured to reconstruct image data based on an output of the radiation detector; and a collimator unit equipped in the radiation source and configured to form the radioactive rays according to a subject to be treated, the collimator unit including a plurality of collimator plates disposed along the rotating axis, each of said plurality of collimator plates having a face on a substantially common plane perpendicular to the beam direction and being individually movable in a length direction perpendicular to the beam direction around an aperture, each collimator plate of said plurality of collimator plates being in direct contact with at least one adjacent collimator plate adjacent in a width direction perpendicular to both the beam direction and the length direction, and a mechanism for selectively moving one or more of said plurality of collimator plates, wherein said plurality of collimator plates includes a plurality of central collimator plates, each central collimator plate of said plurality of central collimator plates having a first X-ray transmittivity along the beam direction, and a plurality of non-central collimator plates, each non-central collimator plate of said plurality of non-central collimator plates having a second X-ray transmittivity along the beam direction, the second X-ray transmittivity being lower than the first X-ray transmittivity, the plurality of non-central collimator plates sandwiching the plurality of central collimator plates, each of the plurality of central collimator plates and each of the plurality of non-central collimator plates having a substantially equal width in the width direction and substantially equal length in the length direction.

2. The concentrated irradiation type radiotherapy apparatus of claim 1, wherein one of the plurality of central collimator plates has a thickness in the beam direction smaller than a thickness in the beam direction of one of the plurality of non-central collimator plates.

* * * * *